United States Patent
Heruth et al.

(10) Patent No.: US 8,244,360 B2
(45) Date of Patent: Aug. 14, 2012

(54) REGIONAL THERAPIES FOR TREATMENT OF PAIN

(75) Inventors: Kenneth T. Heruth, Edina, MN (US); Mark S. Lent, Brooklyn Park, MN (US); Ruchika Singhal, Minneapolis, MN (US); Michael J. Schendel, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1562 days.

(21) Appl. No.: 11/374,793

(22) Filed: Mar. 14, 2006

(65) Prior Publication Data

US 2007/0039625 A1 Feb. 22, 2007

Related U.S. Application Data

(60) Provisional application No. 60/700,627, filed on Jul. 19, 2005, provisional application No. 60/761,823, filed on Jan. 25, 2006.

(51) Int. Cl.
*A61N 1/32* (2006.01)
(52) U.S. Cl. .......................................... 607/46; 607/45
(58) Field of Classification Search ............... 607/45–46
See application file for complete search history.

(56) References Cited

U.S. PATENT DOCUMENTS

| | | | |
|---|---|---|---|
| 5,458,631 A | 10/1995 | Xavier | |
| 5,466,247 A | 11/1995 | Scheiner et al. | |
| 5,782,798 A | 7/1998 | Rise | |
| 6,014,588 A | 1/2000 | Fitz | |
| 6,038,480 A | 3/2000 | Hrdlicka et al. | |
| 6,058,331 A | 5/2000 | King | |
| 6,094,598 A | 7/2000 | Elsberry et al. | |
| 6,128,537 A | 10/2000 | Rise | |
| 6,208,902 B1 | 3/2001 | Boveja | |
| 6,314,325 B1 | 11/2001 | Fitz | |
| 6,473,653 B1 | 10/2002 | Schallhorn et al. | |
| 6,505,075 B1 | 1/2003 | Weiner | |
| 6,662,051 B1 | 12/2003 | Eraker et al. | |
| 6,701,190 B2 | 3/2004 | Gliner | |
| 6,735,474 B1 | 5/2004 | Loeb et al. | |
| 6,735,475 B1 | 5/2004 | Whitehurst et al. | |
| 6,871,099 B1 | 3/2005 | Whitehurst et al. | |

(Continued)

FOREIGN PATENT DOCUMENTS

FR 2 792 844 11/2000

(Continued)

OTHER PUBLICATIONS

Kapural et al., "Occipital Nerve Electrical Stimulation via the Midline Approach and Subcutaneous Surgical Leads for Treatment of Severe Occipital Neuralgia: A Pilot Study," Anesthesia Analgesia 2005; 101, pp. 171-174.

(Continued)

*Primary Examiner* — Niketa Patel
*Assistant Examiner* — Joseph Stoklosa
(74) *Attorney, Agent, or Firm* — Shumaker & Sieffert, P.A.

(57) ABSTRACT

Systems and methods for coordinated delivery of a therapeutic agent and low (less than about 20 Hz) and high (greater than about 50 Hz) frequency stimulation therapy are described. The systems include a control unit for coordinating therapy delivery between an infusion device and a pulse generator, such that a therapeutic agent is administered at a predetermined time relative to application of either low frequency or high frequency stimulation. For example, the control unit may instruct the infusion device to deliver therapeutic agent at a predetermined time prior to delivery of low frequency stimulation. Systems that include more than one infusion device or an infusion pump capable of delivering more than one therapeutic agent are also described.

21 Claims, 30 Drawing Sheets

U.S. PATENT DOCUMENTS

| | | | |
|---|---|---|---|
| 6,988,006 | B2 | 1/2006 | King et al. |
| 7,010,345 | B2 | 3/2006 | Hill et al. |
| 7,010,351 | B2 | 3/2006 | Firlik et al. |
| 2002/0107553 | A1 | 8/2002 | Hill et al. |
| 2002/0143369 | A1 | 10/2002 | Hill et al. |
| 2002/0165586 | A1 | 11/2002 | Hill et al. |
| 2002/0198572 | A1 | 12/2002 | Weiner |
| 2003/0004549 | A1 | 1/2003 | Hill et al. |
| 2003/0078633 | A1 | 4/2003 | Firlik et al. |
| 2003/0100931 | A1 | 5/2003 | Mullett |
| 2003/0144709 | A1 | 7/2003 | Zabara et al. |
| 2003/0204274 | A1 | 10/2003 | Ullestad et al. |
| 2003/0212445 | A1 | 11/2003 | Weinberg |
| 2004/0015202 | A1 | 1/2004 | Chandler, III et al. |
| 2004/0082908 | A1 | 4/2004 | Whitehurst et al. |
| 2004/0122477 | A1 | 6/2004 | Whitehurst et al. |
| 2004/0133390 | A1 | 7/2004 | Osorio et al. |
| 2004/0220544 | A1 | 11/2004 | Heruth et al. |
| 2004/0230229 | A1 | 11/2004 | Lovett et al. |
| 2005/0015117 | A1 | 1/2005 | Gerber |
| 2005/0070948 | A1 | 3/2005 | Kirsteins |
| 2005/0070969 | A1 | 3/2005 | Gerber |
| 2005/0143789 | A1 | 6/2005 | Whitehurst et al. |
| 2005/0228451 | A1 | 10/2005 | Jaax et al. |
| 2005/0246006 | A1 | 11/2005 | Daniels |
| 2005/0277999 | A1 | 12/2005 | Strother et al. |
| 2006/0047325 | A1 | 3/2006 | Thimineur et al. |

FOREIGN PATENT DOCUMENTS

| | | |
|---|---|---|
| WO | WO 00/15293 | 3/2000 |
| WO | WO 01/02054 | 1/2001 |
| WO | WO 01/89626 | 11/2001 |
| WO | WO 02/34330 | 5/2002 |
| WO | WO 02/068042 | 9/2002 |
| WO | WO 03/026736 | 4/2003 |
| WO | WO 03/047687 | 6/2003 |
| WO | WO 2004/012812 | 2/2004 |

OTHER PUBLICATIONS

Notification of Transmittal of the International Search Report and the Written Opinion for corresponding PCT Application No. PCT/US2006/022519, dated Dec. 27, 2006 (13 pgs.).

Reply to Written Opinion for corresponding PCT Application No. PCT/US2006/022519 dated Apr. 9, 2007 (4 pgs.).

Notification of Transmittal of the International Preliminary Report on Patentability for corresponding PCT Application No. PCT/US2006/022519, dated Sep. 28, 2007 (8 pgs.).

U.S. Appl. No. 11/450,133, filed Jun. 9, 2006, entitled "Combination Therapy Including Peripheral Nerve Field Stimulation."

U.S. Appl. No. 11/450,127, filed Jun. 9, 2006, entitled "Implantable Medical Device with Electrodes on Multiple Housing Surfaces."

U.S. Appl. No. 11/450,147, filed Jun. 9, 2006, entitled "Introducer for Therapy Delivery Elements."

U.S. Appl. No. 11/450,144. filed Jun. 9, 2006, entitled "Peripheral Nerve Field Stimulation and Spinal Cord Stimulation."

U.S. Appl. No. 11/450,148, filed Jun. 9, 2006, entitled "Implantable Medical Lead."

U.S. Appl. No. 11/374,852, filed Mar. 14, 2006, entitled "Regional Therapies for Treatment of Pain."

U.S. Appl. No. 11/375,492, filed Mar. 14, 2006, entitled "Regional Therapies for Treatment of Pain."

Ghoname, et al., Percutaneous Electrical Nerve Stimulation for Low Back Pain, Mar. 3, 1999, p. 818-823, vol. 281, No. 9, JAMA.

Remington'S Pharmaceutical Sciences, Ch. 43, 14$^{th}$ Ed.

Schwartz, et al., Electric Sympathetic Block: Methods of Measurement and a Study Assessing Its Effectiveness, Adv. Ther., Sep./Oct. 1990, p. 289-291, vol. 7, No. 5.

Loh, et al., Painful Peripheral States and Sympathetic Blocks, J Neurol Neurosurg Psychiatry, Jul. 1978, p. 664-671, vol. 7, No. 5.

Loh, et al., Pain Due to Lesions of Central Nervous System Removed by Sympathetic Block, Mar. 1981, p. 1026-1028, vol. 282, No. 6269.

Connally, et al., Predicting Low Back Pain Patients' Response to Lumbar Sympathetic Nerve Blocks and Interdisciplinary Rehabilitation . . . , Feb. 1991, p. 139-146, vol. 44, No. 2.

Sluka, et al., High-Frequency, But Not Low-Frequency, Transcutaneous Electrical Nerve Stimulation Reduces Aspartate . . . , J Neurochem, Oct. 2005, p. 1794-1801, vol. 95.

Kalra, Blockade of Opioid Receptors in Rostral Ventral Medulla Prevents Antihyperalgesia Produced by Transcutaneous . . . , J Pharmacol Exp Ther, Jul. 2001, p. 257-263, vol. 298, No. 1.

Sluka, et al., Spinal Blockage of Opioid Receptors Prevents the Analgesia Produced by TENS in Arthritic Rats, J Pharmacol Exp Ther, May 1999, p. 840-846, vol. 289, No. 2.

Hassenbusch, et al., Polyanalgesic Consensus Conference 2003: An Update on the Management of Pain by Intraspinal Drug Delivery . . . , J of Pain and Symptom Mgmt, Jun. 2004, p. 540-563, vol. 27, No. 6.

Radhakrishnan, et al., Spinal Muscarinic Receptors are Activated During Low or High Frequency TENS-Induced Antihyperalgesia in Rats, Neuropharmacology, Dec. 2003, p. 1111-1119, vol. 45, No. 8.

Gopalkrishnan, et al., Effect of Varying Frequency, Intensity, and Pulse Duration of Transcutaneous Electrical Nerve Stimulation . . . , Arch Phys Med Rehab, Jul. 2000, p. 984-990, vol. 81, No. 7.

Sluka, et al., Treatment with Either High or Low Frequency TENS Reduces the Secondary Hyperalgesia Observed After Injection of Kaolin and Carrageenan into the Knee Joint, Pain, Jul. 1998, p. 97-102, vol. 77, No. 1.

Sluka, et al., Low Frequency TENS is Less Effective than High Frequency TENS at Reducing Inflammation-Induced Hyperalgesia in Morphine-Tolerant Rats, Eur J Pain, 2000, p. 185-193, vol. 4, No. 2.

Ma, et al., Reduction in Inflammation-Induced Sensitization of Dorsal Horn Neurons by Transcutaneous Electrical Nerve Stimulation in Anesthetized Rats, Exp Brain Res, Mar. 2001, p. 94-102, vol. 137, No. 1.

Chandran, et al., Development of Opioid Tolerance with Repeated Transcutaneous Electrical Nerve Stimulation Administration, Pain, Mar. 2003, p. 195-201, vol. 102, No. 1.

Sluka, et al., Enhanced Reduction in Hyperalgesia by Combined Administration of Clonidine and TENS, Pain, Nov. 2002, p. 183-190, vol. 100, No. 1-2.

Radhakrishnan, et al., Spinal 5-HT(2) and 5-HT(3) Receptors Mediate Low, but not High, Frequency TENS-Induced . . . , Pain, Sep. 2003, p. 205-213, vol. 105, No. 1-2.

Sluka, et al., Transcutaneous Electrical Nerve Stimulation: Basic Science Mechanisms and Clinical Effectiveness, J Pain, Apr. 2003, p. 109-121, vol. 4, No. 3.

King, et al., The Effect of Varying Frequency and Intensity of Transcutaneous Electrical Nerve Stimulation on Secondary Mechanical . . . , J Pain, Apr. 2001, p. 128-133, vol. 2, No. 2.

Radhakrishnan, et al., Deep Tissue Afferents, but Not Cutaneous Afferents, Mediate Transcutaneous Electrical Nerve Stimulation . . . , J Pain, Oct. 2005, p. 673-680, vol. 6, No. 10.

Office Action dated Feb. 1, 2008 for U.S. Appl. No. 11/375,492 (9 pgs.).

Responsive Amendment dated May 30, 2008 for U.S. Appl. No. 11/375,492 (18 pgs.).

Office Action dated Jan. 23, 2008 for U.S. Appl. No. 11/374,852 (8 pgs.).

Responsive Amendment dated May 23, 2008 for U.S. Appl. No. 11/374,852 (17 pgs.).

Bedder "Implantable delivery Systems," http://web.archive.org/web/20050428002533/http://www.imiworkshops.com/pdfs/articles/general/implant_systems.pdf, Apr. 28, 2005 (11 pgs.).

Office Action dated Sep. 3, 2008 for U.S. Appl. No. 11/374,852 (8 pgs.).

Responsive Amendment dated Dec. 3, 2008 for U.S. Appl. No. 11/374,852 (18 pgs.).

Office Action dated Sep. 4, 2008 for U.S. Appl. No. 11/375,492 (9 pgs.).

Responsive Amendment dated Dec. 4, 2008 for U.S. Appl. No. 11/375,492 (16 pgs.).

Office Action dated Apr. 6, 2009 for U.S. Appl. No. 11/375,492 (9 pgs.).

Responsive Amendment dated Jul. 1, 2009 for U.S. Appl. No. 11/375,492 (16 pgs.).

Office Action dated Aug. 18, 2009 for U.S. Appl. No. 11/374,852 (12 pgs.).

Responsive Amendment dated Oct. 19, 2009 for U.S. Appl. No. 11/374,852 (11 pgs.).
Responsive Amendment dated Nov. 16, 2009 for European Application 06772721.4 (11 pgs.).
Office Action dated Feb. 20, 2009 for U.S. Appl. No. 11/374,852 (10 pgs.).
Responsive Amendment dated May 20, 2009 for U.S. Appl. No. 11/374,852 (16 pgs.).
Response to Office Action mailed Oct. 18, 2011 for European Application No. 06772721.4, (5 pgs.).
Office Action dated Feb. 18, 2010 for U.S. Appl. No. 11/375,492 (10 pgs.).
Response dated Apr. 15, 2010 for U.S. Appl. No. 11/375,492 (9 pgs.).
Office Action dated Jun. 15, 2011 for European Application No. 06772721.4, (3 pgs.).

BACKGROUND

BACKGROUND

BACKGROUND

BACKGROUND

BACKGROUND

REGIONAL THERAPIES FOR TREATMENT OF PAIN

RELATED APPLICATIONS

This application claims the benefit of priority to U.S. Provisional Patent Application Ser. Nos. 60/700,627, filed on Jul. 19, 2005 and 60/761,823, filed on Jan. 25, 2006, which applications are incorporated herein by reference in their entireties. This application also claims the benefit of priority to U.S. Provisional Application Ser. Nos. 60/689,168, 60/689,201, 60/689,202, 60/689,203 and 60/689,204, each of which was filed on Jun. 9, 2005.

FIELD

The following disclosure relates generally to medical devices and methods for treating of pain with implantable medical devices.

BACKGROUND

Pain can be a debilitating disorder that is difficult to treat. Much of the difficulty in treating pain may be associated with the varying physiological bases for different types of pain and may be due to the rather complex neurological basis for each type of pain. While complex, a great deal is known about pain transmission at the cellular and molecular level.

Referring to FIG. 1, a variety of neuronal cell types may be involved in the transmission or perception of pain. For example, Aβ, Aδ, and C primary afferent 10 fibers transmit signals from the periphery to the spinal cord 20. Cell bodies of the neurons with these fibers lie in dorsal root ganglion 30 and their axons pass through dorsal roots 40 prior to synapsing in the dorsal horn 50 of the spinal cord 20. More specifically, branches of these axons may ascend or descend a few vertebral segments in the tract of Lissauer, and axon collaterals may synapse with many neurons in the dorsal horn 50. These afferents 10 may synapse with inhibitory interneurons 500 or projection neurons 510 that send ascending projections through various ascending tracts 60 (see FIG. 2), such as the spinothalamic tract, the spinoreticular tract, the spinomesencephalic tract, or the spinocervical tract. The various ascending tracts 60 send projections to the thalamus or other midbrain structures.

For example, spinothalamic tract projection neurons may terminate in the medial nuclear group of the thalamus, including the central lateral nucleus and the ventral posterior lateral nucleus; spinoreticular tract projection neurons may terminate in the reticular formation of the pons or the thalamus; spinomesencephalic tract neurons may project to the mesencephalic reticular formation, the lateral part of the periaqueductal gray region, and other midbrain structures; and spinocervical tract neurons may project to midbrain nuclei and the thalamus, including the ventroposterior lateral and posterior medial nuclei. In these higher centers, in other regions of the brain receiving projections from these centers, or combinations thereof, pain may be perceived.

Descending fibers originating from, e.g., the periaqueductal gray matter, the nucleus raphe magnus or the nucleus paragigantocellularis, send projections in descending tracts 70 in the dorsolateral funiculus, directly or indirectly, to the dorsal horn 50 of the spinal cord 20, where they may synapse with interneurons or ascending projection neurons. The descending neurons that synapse with neurons in the dorsal horn 50 of the spinal cord are typically serotoninergic or noradrenergic neurons and may act to suppress activity of ascending projection neurons, especially those involved with nociception. Due in part to the large number of classes of neurons involved in pain transmission and perception, pain can be difficult to treat. In addition, pain may have different origins in different patients, making pain therapy management and strategy difficult. For example, some patients may benefit from inhibition of C fiber activity alone. Others may benefit from inhibition of Aβ fibers. Some may benefit from increased activity of Aα/Aβ fibers and descending neurons.

Further complicating the treatment of pain is the involvement of sympathetic neurons. Sympathetic neurons include projections in the spinal cord that originate from the brain to interneurons or to preganglionic neurons, interneurons, preganglionic neurons and postganglionic neurons. Sympathetic projections from the brain including brain stem, midbrain and forebrain to preganglionic sympathetic neurons or interneurons of the spinal cord include projections from brain areas such as the paraventricular nucleus of the hypothalamus, rostral ventrolateral medulla, ventromedial medulla, and caudal raphe nucleus. Preganglionic cell bodies of the sympathetic nerves and associated interneurons generally reside within the intermediolateral cell column of the lateral horn 80 of the spinal cord 20 at C1-S5. Generally, preganglionic sympathetic cell bodies send projections that exit the spinal cord through the ventral roots 90 to synapse with postganglionic neurons in sympathetic ganglia 100. Examples of sympathetic ganglia 100 include not only the chain of ganglia on each side of the spinal column, but also the inferior mesenteric, superior mesenteric, celiac, submandibular, otic, and pterygopalatine ganglia. Postganglionic nerves send projections that typically follow the vasculature to innervate end organs. Activity of sympathetic efferent fibers following peripheral nerve injury may cause burning pain, e.g., causalgia, or reflex sympathetic dystrophy syndrome. This activity is thought to cause pain by direct activation of damaged nociceptive afferent neurons or by nonsynaptic sympathetic transmission.

The sympathetic nervous system also comprises afferent fibers 140, which pass from the peripheral sympathetic system through the rami communicantes. Some of these fibers terminate about cell bodies within dorsal root ganglia 30. Cell bodies of some sympathetic afferents may be located in dorsal root ganglia 30 or sympathetic ganglia 100. Those ending in sympathetic ganglia 100 may send projections, direct or indirect to the lateral column 80 of the spinal cord 20. Shown in FIG. 1 are sympathetic afferent fibers, which project from discs 110 through sympathetic trunks via sympathetic ganglia 100 enter the spinal cord 20 through dorsal roots 40. Nerve endings in the vertebral discs are generally located in peripheral third of the disc.

Increased sympathetic activity has been implicated in increased pain in some circumstances and blocking of sympathetic neurons with drugs or electrical stimulation has been used to treat or prevent acute pain. In addition, RF and surgical lesions of the sympathetic chain are used to treat chronic pain. However, these are non-reversible therapies and may be difficult to repeat.

In addition to synapsing on inhibitory interneurons 500 and/or projection neurons 510, neurons of Aβ, Aδ, and C primary afferent fibers 10 may synapse on sympathetic efferent neurons 600 (see, e.g., FIG. 3). The connections between afferent inputs to the spinal cord and sympathetic efferent outputs may be an important target in the treatment of pain.

Spinal cord stimulation (SCS), while not perfect, has been useful for treating pain. The precise mechanism of action of SCS is not fully understood. As shown in FIG. 4, SCS typically involves stimulation via one or more epidurally placed electrode of a lead 120. FIG. 5 shows an alternative perspective view of a portion of a spinal cord 20 with epidural placement of a lead 120. In both FIG. 4 and FIG. 5, the lead 120 and its associated electrode(s) are positioned epidurally near the dorsal columns. A depolarizing electrical signal is delivered through the electrode(s). In theory, the depolarizing electrical signal excites ascending neurons 700 in the dorsal columns. The ascending neurons 700 in the dorsal column send collaterals that synapse with neurons in the dorsal horn 50, including primary afferents, inhibitory interneurons 500, and/or projection neurons 510. Stimulation of the dorsal column may to a lesser extent excite neurons in the descending tract 70, thereby enhancing the pain inhibiting effects of the descending transmissions. In addition, epidural SCS recruits large fibers, such as Aβ fibers, which can excite inhibitory interneurons 500 in the dorsal horn 50, thereby inhibiting transmission of pain signals through projection neurons 510 that run in ascending tracts 60. While lead 120 placement is in proximity to the dorsal columns, the effects of such electrical stimulation may spread to the dorsal roots 40 through the relatively conductive cerebrospinal fluid (CSF). Thus as described above, primary afferent Aβ fibers may be recruited and at least a portion of the treatment of pain may be due to effects on neurons in the dorsal roots 40. However, it is possible that the efficacy of such treatment is attenuated by effects at the dorsal roots 40 through stimulation of, e.g., C-fibers.

The efficacy of epidural electrical stimulation of the dorsal column can be quite high immediately after lead placement, e.g. approximately 60% for low back pain. However, within a few months the efficacy may drop as tolerance develops. For example, efficacy of dorsal SCS for treatment may drop to as little as 20% after about six months. The mechanisms for the development for such tolerance are not well understood. In addition to tolerance, epidural stimulation suffers from increased energy needs for the stimulation signal to cross the dura 130 and loss or inadvertent stimulation of dorsal roots due to CSF conductance.

Transcutaneous electrical neural stimulation (TENS) is another potential therapy for treatment of pain that has been shown to work well in rodent models. Many of such animal models involve artificially induced inflammation in a knee joint of a rat where TENS therapy is applied to the knee. Such models have shown that high frequency TENS is effective for treatment of primary and secondary hyperalgesia as well as morphine-tolerant secondary hyperalgesia, while low frequency TENS is effective for secondary hyperalgesia but not morphine-tolerant secondary algesia or primary hyperalgesia. In addition, much has been learned from such models about the mechanisms and interactions between peripheral pain and peripherally-applied TENS to central pain neurotransmission. For example, the effect of peripherally-applied TENS on central opioid, serotonin, muscarinic, and noradrenergic neurotransmission has become better understood. However, to date, TENS has not yet been shown to be consistently effective in treatment of pain, particularly low back pain. For low back pain, TENS may be impracticable as rather large leads and electrodes would likely be needed to provide a sufficient stimulation signal to deeper areas such as sympathetic ganglia 100 and dorsal roots 40. In addition, a TENS signal capable of stimulating such deeper structures in humans is also likely to stimulate unintended neurons causing side effects.

Accordingly, there remains a need for additional therapies to treat pain. Preferably such therapies increase efficacy over existing therapies or reduce tolerance relative to existing therapies.

SUMMARY

Embodiments of the present invention relate to implantable medical devices, systems and methods for coordinating therapy delivery between a pulse generator and an infusion device. In various embodiments, systems comprise a pulse generator and an infusion device that coordinate delivery of stimulation therapy and therapeutic agent infusion. The pulse generator and infusion pump may be in communication or may be instructed to provide therapy in a coordinated fashion. The systems may comprise a control unit, which may be housed with the pulse generator or infusion device or may be housed separately from the pulse generator or infusion pump, to coordinate the therapy.

In an embodiment, the invention provides a system. The system comprises a pulse generator capable of alternating between generation of a first electrical signal and generation of a second electrical signal. The system further comprises first infusion device capable of delivering a therapeutic agent at a rate at a predetermined time based on when the pulse generator switches from generation of the first signal to generation of the second signal. In addition, the system comprises a control unit configured to coordinate the delivery of the therapeutic agent at the rate from the infusion device with the switch from the generation of the first signal to the generation of the second signal.

In an embodiment, the invention provides a system that comprises (i) a pulse generator capable of alternating between generation of a first electrical signal and generation of a second electrical signal, and (ii) an infusion device capable of initiating delivery of a therapeutic agent at a rate during a time when the pulse generator generates the first signal and ceasing delivery of the therapeutic agent at the rate during a time when the pulse generator generates the second signal. The system further comprises a control unit configured to coordinate the initiation of delivery of the therapeutic agent from the infusion device with the generation of the first signal and the cessation of delivery of the first therapeutic agent from the first infusion device with the generation of the second signal.

In an embodiment, the invention provides a system that comprises an infusion device capable of delivering a therapeutic agent at a predetermined rate and a pulse generator capable of generating a first electrical signal and a second electrical signal. The system further comprises a control unit configured to coordinate generation of the first electrical signal by the pulse generator during a time when the infusion device is delivering the therapeutic agent at the predetermined rate and generation of the second electrical signal by the pulse generator at a time when the infusion device is delivering the therapeutic agent at a rate other than the predetermined rate.

In an embodiment, the invention provides a system comprising means for delivering to a subject a first therapeutic agent, means for delivering to the subject a first electrical signal having a first frequency, means for controlling whether the first or second electrical signal is delivered to the subject, and means for controlling timing of the administration of an amount of the first therapeutic agent based on whether the first or second electrical signal is being delivered.

In an embodiment, the invention provides a system comprising a pulse generator capable of alternating between generation of a first electrical signal and generation of a second electrical signal and an infusion device configured to deliver a therapeutic agent at a predetermined time from when the pulse generator switches from generation of the first signal to generation of the second signal.

In an embodiment, the invention provides a method that comprises identifying whether a first predetermined electrical signal is being generated by an implantable pulse generator and instructing an infusion device to deliver a therapeutic agent at a rate if the predetermined electrical signal is being generated.

In an embodiment the invention provides a method that comprises instructing an implantable pulse generator to generate a first and a second electrical signal at predetermined times and instructing an infusion device to deliver a therapeutic agent at a predetermined time relative to generation of the first or second electrical signal.

Various embodiments of the invention provide one or more advantages over existing treatment systems and therapies. The coordinated delivery of therapeutic agent with particular stimulation parameters may provide increased efficacy and reduced tolerance. For example, the coordinated administration of one or more pain treating agent with high or low frequency stimulation should enhance efficacy of either treatment given alone. In addition, with proper timing of delivery of pain treating agent and combination with appropriate stimulation, the amount of pain treating agent to be delivered may be reduced so that tolerance may be reduced. These and other advantages will be evident in light of the description and figures that follow.

BRIEF DESCRIPTION OF THE DRAWINGS

In the following description, reference is made to the accompanying drawings that form a part hereof, and in which are shown by way of illustration several specific embodiments. It is to be understood that other embodiments are contemplated and may be made without departing from the scope or spirit of the teachings of this disclosure. The following description, therefore, is not to be taken in a limiting sense.

FIG. 23B shows the inclusion of a control unit.

Figure 1:
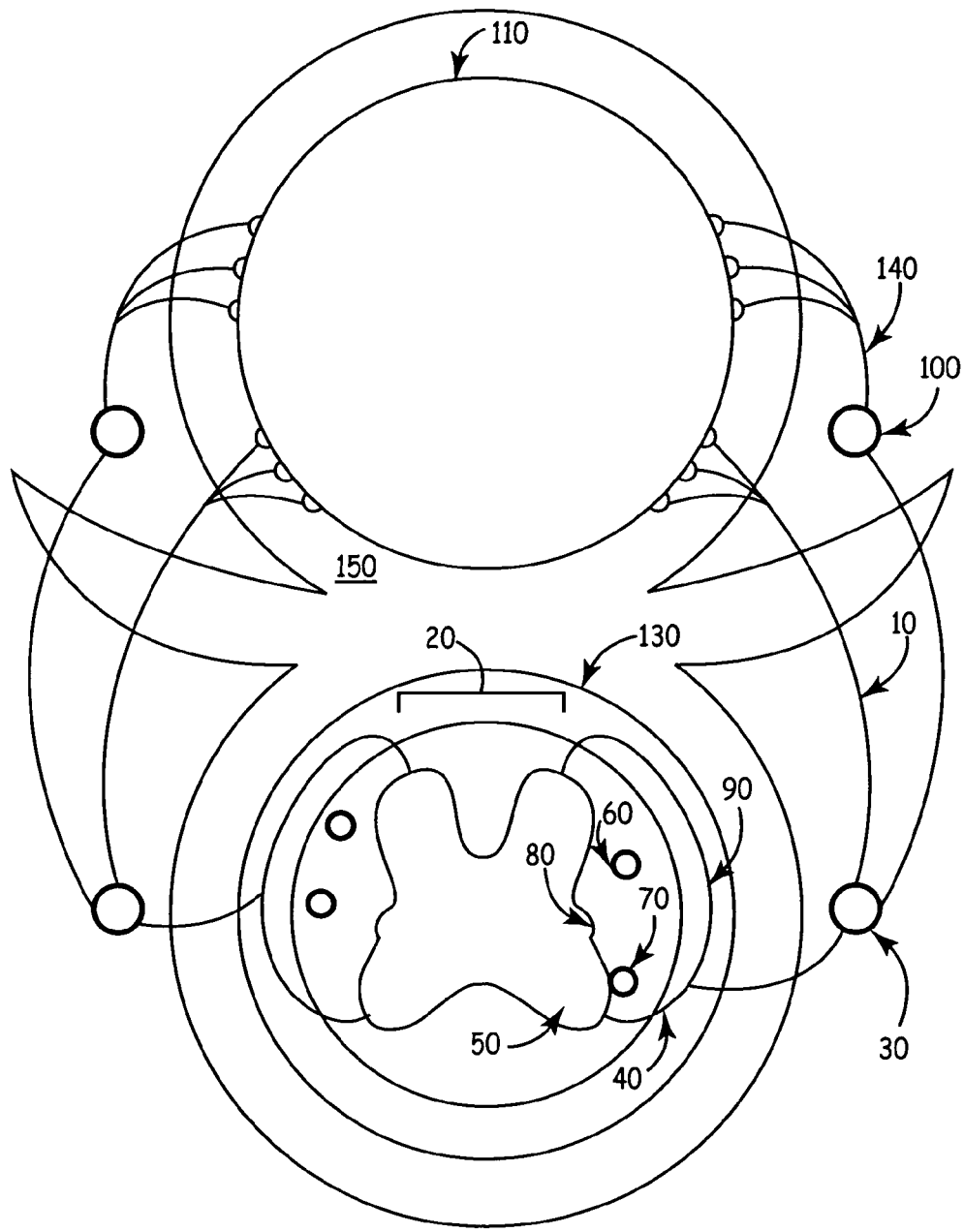
FIG. 1 is a diagrammatic representation of a cross section of a spinal cord with selected nerve fibers and neurons shown.
Figure 2:
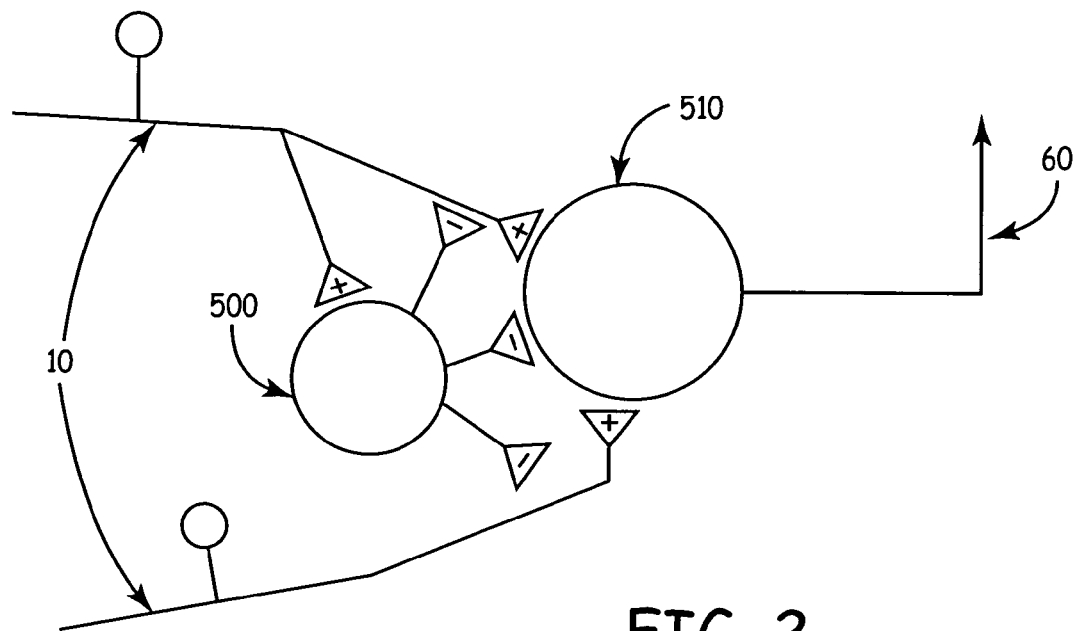
FIG. 2 is a schematic view of afferents synapsing with inhibitory interneurons or projection neurons in a spinal cord.
Figure 3:
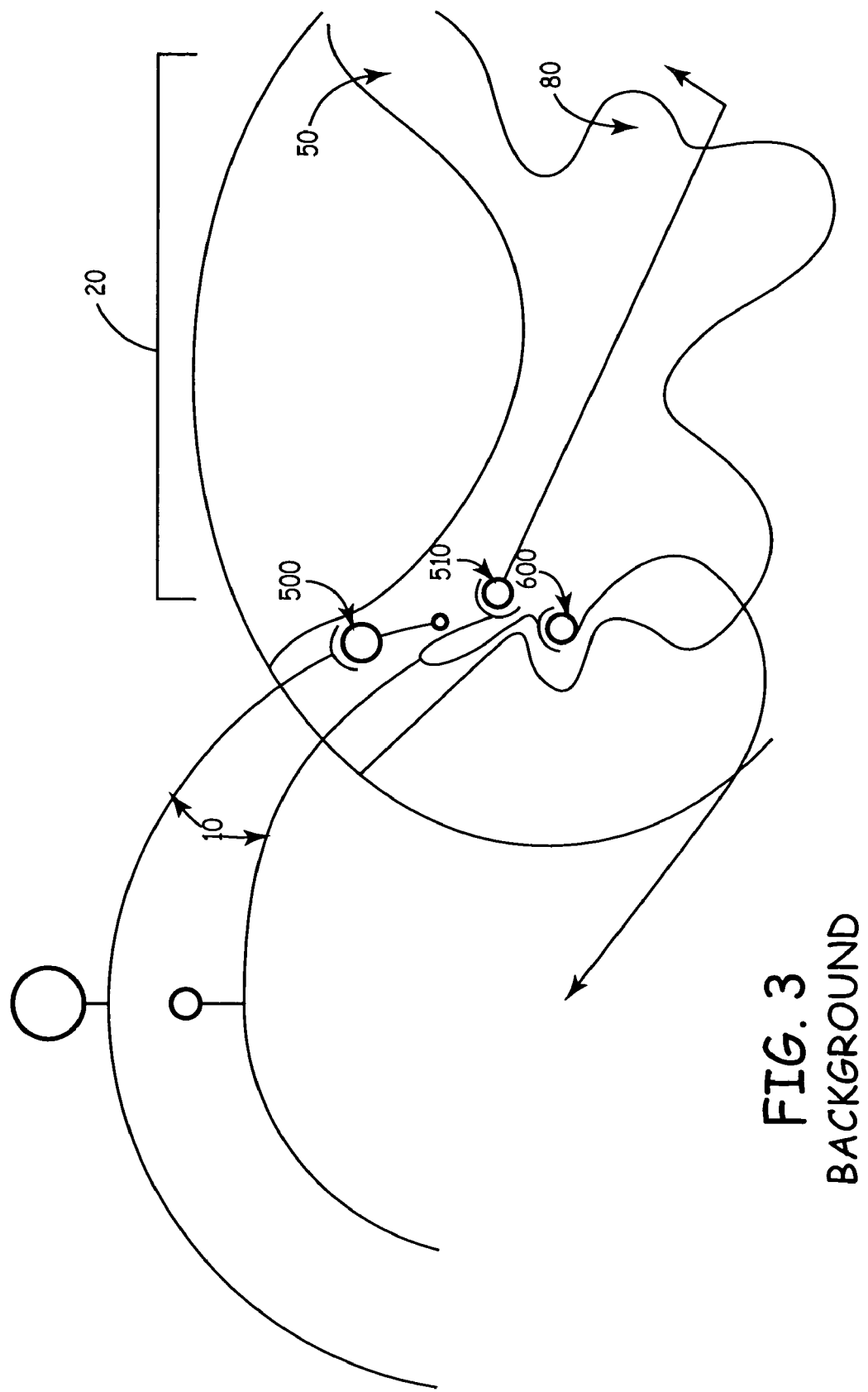
FIG. 3 is a diagrammatic representation of a cross section of a spinal cord with selected nerve fibers and neurons shown.
Figure 4:
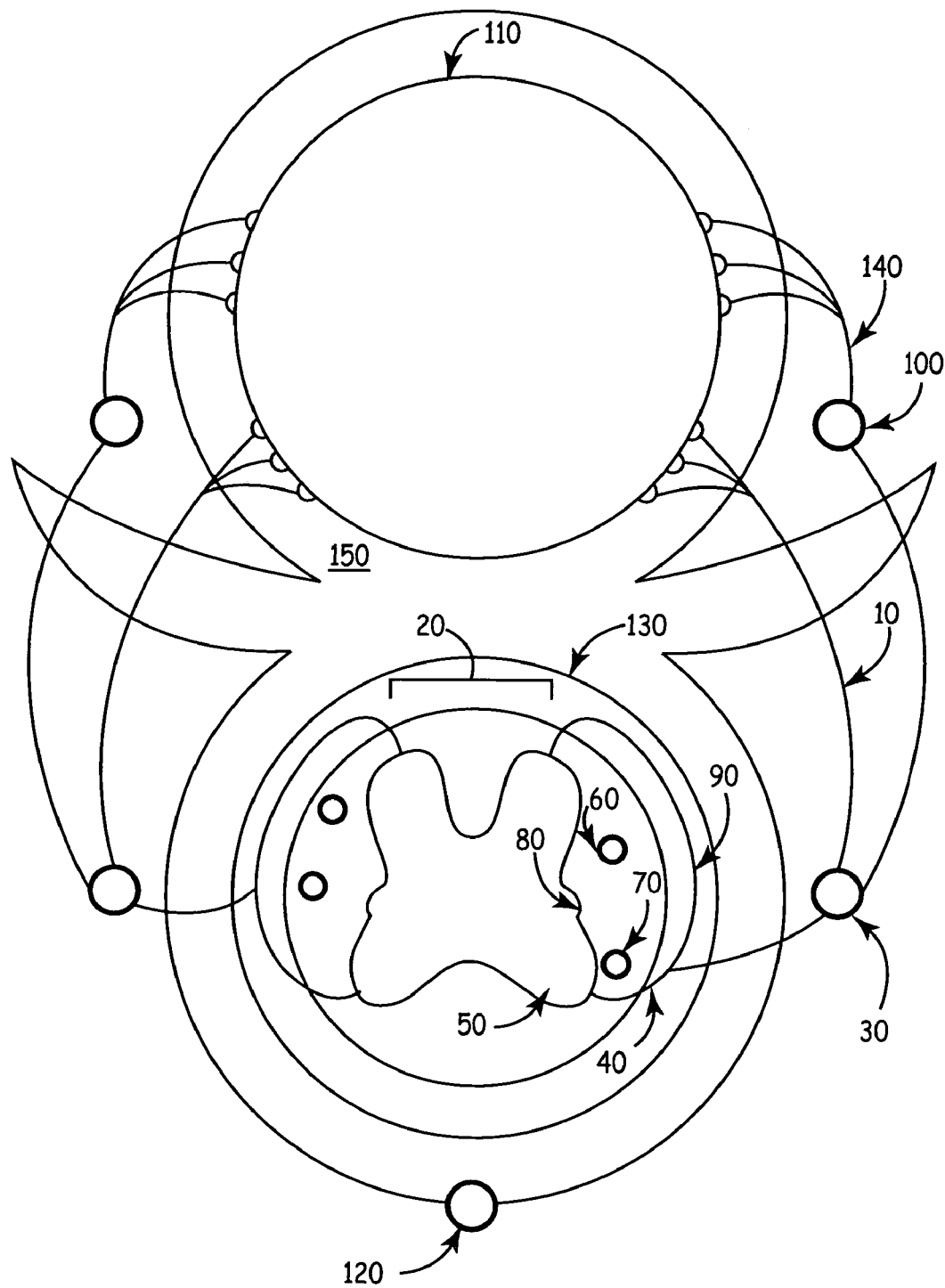
FIG. 4 is a diagrammatic representation of a cross section of a spinal cord with selected nerve fibers and neurons and an epidurally placed lead shown.
Figure 5:
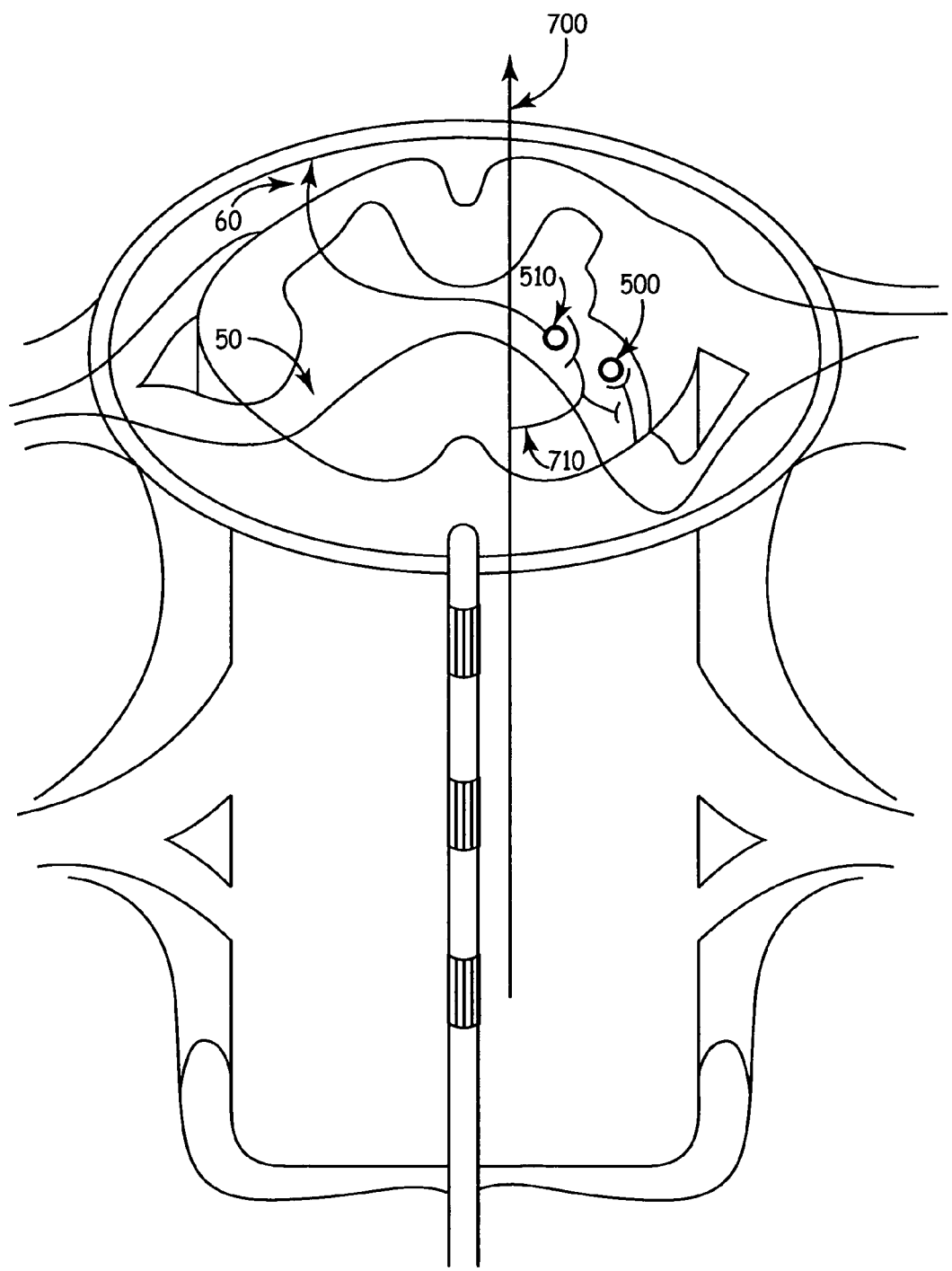
FIG. 5 is a diagrammatic representation of a perspective view of a spinal cord with selected nerve fibers and neurons and an epidurally placed lead shown.

The drawings are not necessarily to scale.

Reference numbers used in the drawings are not intended to limit a particular feature of a device, system or method. For example, even though reference number 5000 refers to an implantable infusion device in FIG. 14, it will be understood that infusion devices that are not implantable can be readily substituted in many of the embodiments discussed. In addition, use of different reference numbers to refer to the same feature, device or method step (e.g., the use of reference numbers 16, 18 and 120 for leads) does not necessarily indicate that the features, devices, or method steps are not the same or similar. For example, reference numbers 16, 18 and 120 refer to leads generally and each may be the same or different model of lead, depending on the context in which it is discussed.

DETAILED DESCRIPTION

In the following description, reference is made to the accompanying drawings that form a part hereof, and in which are shown by way of illustration several embodiments of the invention. It is to be understood that other embodiments are contemplated and may be made without departing from the scope or spirit of the present invention. The following detailed description, therefore, is not to be taken in a limiting sense. Instead, the scope of the invention is to be defined in accordance with the appended claims.

The disclosure provided herein relates generally to apparatuses, systems, and methods for treating pain. The apparatuses, systems, and methods include application of electrical stimulation via one or more implantable electrode. At least one electrode is implanted subcutaneously in proximity to a source of pain of a patient. The electrical stimulation may be applied to a broad region of tissue. The stimulation may contain high frequency or low frequency components and may vary between high and low frequency stimulation. The apparatuses, systems, and methods also include administering a pain treating agent to the subject. The timing and rate of administration of the pain treating agent may be tailored and controlled relative to the timing of the application of electrical stimulation to enhance therapy. The pain treating agent may be administered via an implantable pump.

Generally speaking, the teachings presented herein are applicable to treatment of any type of pain. For exemplary purposes, back pain will be discussed in greater detail herein than pain originating from other regions of the body.

Application of an electrical signal to subcutaneous regions for treatment of pain in humans may allow for some of the benefits associated with TENS therapy as applied to animal models of pain. However, as opposed to TENS therapy, subcutaneous stimulation may allow for finer control of the cells to be stimulated, thereby reducing potential undesired effects relative to TENS. In addition, application of high and low frequency stimulation results in more effective therapy for a wider variety of types of pain, and alternating between high and low frequency stimulation may result in reduced tolerance relative to typical SCS. Further, control of what subcutaneous structures, including the spinal column, receive high or low frequency stimulation may be achieved by subcutaneous placement of electrodes. Subcutaneous placement of electrodes may also allow for a broader area of stimulation than SCS and may result in increased efficacy for treating pain.

The additional application of a pain treating agent may further enhance efficacy of the pain treatment. The efficacy may further be enhanced by controlling the timing of the administration of the pain treating agent relative to the timing of the electrical stimulation. Devices and systems capable of delivering therapeutic agents at predetermined times relative to application of either high or low frequency stimulation also offer advantages relative to currently available systems and methods.

DEFINITIONS

All scientific and technical terms used in this application have meanings commonly used in the art unless otherwise specified. As used in this application, the following words or phrases have the meanings specified.

As used herein "electrical stimulation" or "stimulation" means application of an electrical signal that may be either excitatory or inhibitory to a muscle or neuron that is directly affected by the signal. It will be understood that an electrical signal may be applied to one or more electrodes with one or more return electrodes.

As used herein "or" means and/or unless specifically or implicitly (such as with a preceding "either") stated otherwise.

As used herein "high frequency" means greater than about 50 Hz. Accordingly, high frequency includes greater than about 150 Hz, between about 50 Hz and about 75 Hz, etc.

As used herein "low frequency" means less than about 20 Hz. Accordingly low frequency includes between about 10 Hz and about 20 Hz, less than about 10 Hz, etc.

As used herein an electrode placed "in proximity to a source of pain" means an electrode placed at a location capable of producing a direct electrical effect on tissue that is the source of pain or tissue that if stimulated would result in reduction in pain. Preferably, the placement is such that a stimulation signal delivered by the electrode affects intended tissue and minimizes effects on unintended tissue. For example, an electrode may be placed in proximity to nerves, muscles, or ligament.

As used herein "in proximity to a structure of the back" means an electrode placed at a location capable of producing a direct electrical effect on the structure of the back to which the electrode is placed in proximity. By way of example, the electrode may be placed about 5 mm or less from a structure of the back. The structures of the back that may be a source of pain or that may result in pain reduction if stimulated, include discs, facet joints, nerve roots or ganglions, sympathetic chain, and the like, as well as ligaments and muscles. As used herein, the spinal cord will not be considered "a structure of the back", but rather will be referred to separately.

As used herein "epidural" means situated upon the dura or in very close proximity to the dura.

As used herein "pain treating agent", "therapeutic agent", and the like mean a therapeutic molecule or composition of ameliorating for alleviating one or more symptoms of intended disease, disorder or condition or improving one or more underlying physiological basis of the disease, disorder or condition. A pain treating agent may treat one or more of nociceptive pain, inflammatory pain, and neuropathic pain. It will be understood that "different" therapeutic agents, as used herein, can refer to the same therapeutic molecule present in a composition at different concentrations.

As used herein "treating pain", "pain treatment", and the like mean alleviating or ameliorating one or more symptoms associated with pain or improving one or more etiological factors associated with pain.

The term "comprises" and variations thereof do not have limiting meaning where these terms appear in the accompanying description and claims. Moreover, unless otherwise specified, "a," "an," "the," and "at least one" are used interchangeably and mean one or more than one. Thus, for example, an infusion device that comprises "a" reservoir can be interpreted to mean that the device includes "one or more" reservoirs.

Stimulation

Figure 6:
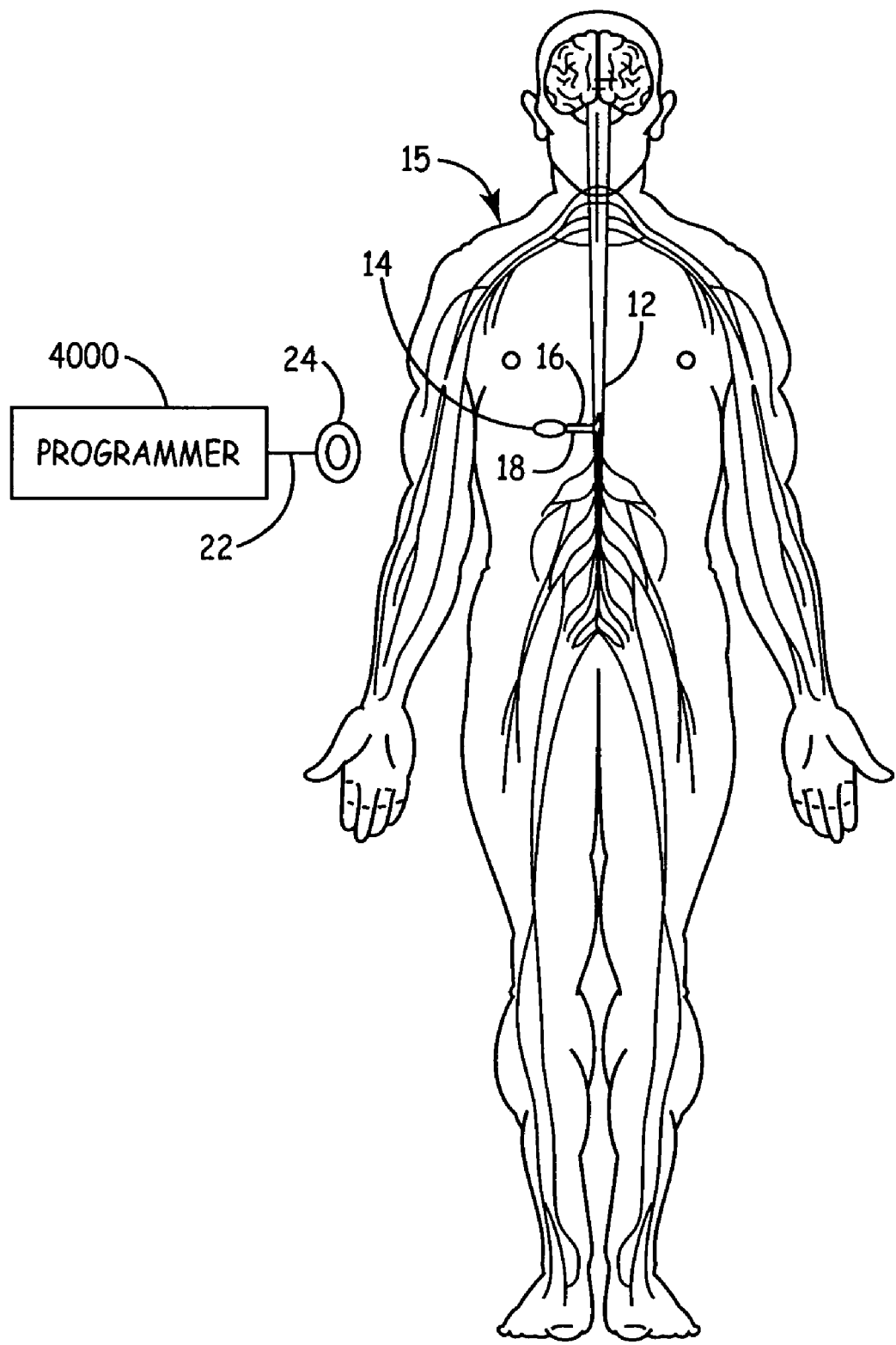
FIG. 6 is a schematic view of a stimulation system implanted in a patient.
Figure 7:
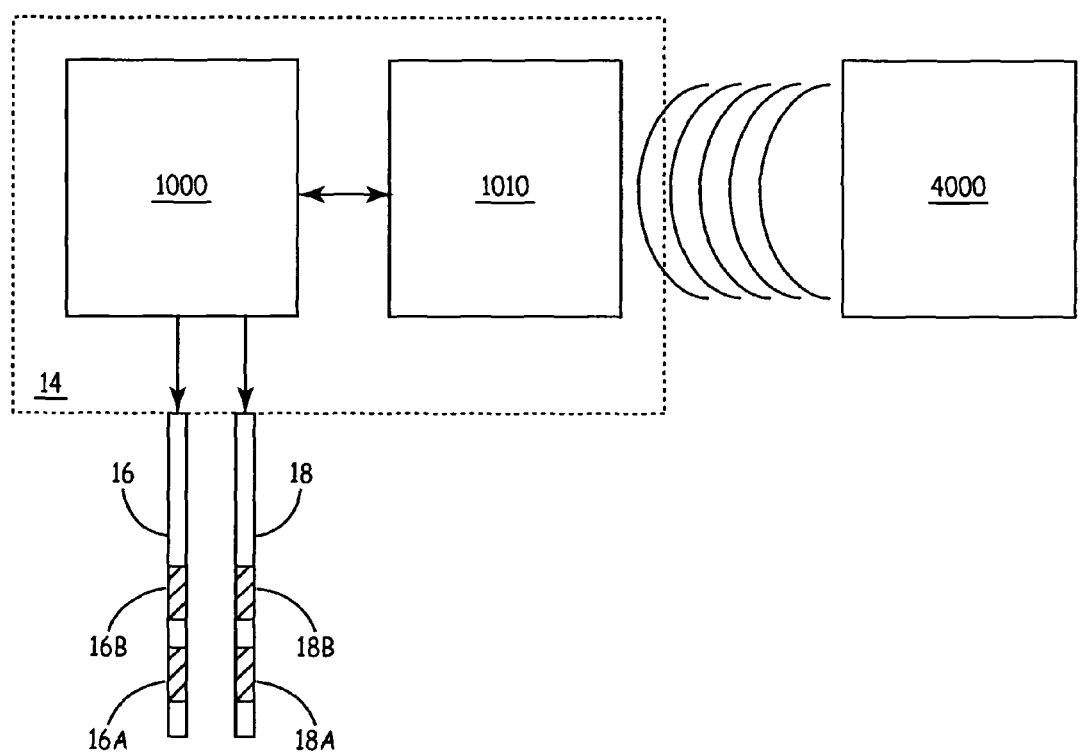
FIG. 7 is a block diagram of an exemplary stimulation system.

Any present or future developed stimulation system capable of providing an electrical signal to one or more regions in proximity to a source of pain of a patient to treat pain may be used in accordance with the teachings provided herein. Referring to FIG. 6, a schematic view of a patient 15 having an implant of an exemplary stimulation system useful for applying an electrical signal in proximity a structure of the back of the patient 15 is shown. The exemplary system employs an implantable pulse generator (IPG) 14 to produce a number of independent stimulation pulses which are sent to a region in proximity to a structure of the back by insulated leads 16 and 18 coupled to the spinal cord by one or more electrodes 16A, 18A (FIG. 7). The one or more electrodes 16A, 18A may be attached to separate conductors included within a single lead. Any known or future developed lead 16, 18 or electrode 16A, 18A useful for applying an electrical stimulation signal in proximity to a patient's 15 spinal cord 12 may be used. For example, the leads 16, 18 may be conventional percutaneous leads, such as PISCES® model 3487A sold by Medtronic, Inc. In certain circumstances it may be desirable to employ a paddle-type lead. Any known or future developed implantable pulse generator may be used in accordance with the teachings of the present disclosure. For example, IPG 14 may be an ITREL® II or Synergy pulse generator available from Medtronic, Inc, Advanced Neuromodulation Systems, Inc.'s Genesis® pulse generator, or Advanced Bionics Corporation's Precision® pulse generator. One of skill in the art will recognize that the above-mentioned pulse generators may be advantageously modified to deliver therapy in accordance with the teachings of this disclosure.

The exemplary system in FIG. 6 employs a programmer 4000 which is coupled via a conductor 22 to a radio frequency antenna 24. This system permits attending medical personnel to select the various pulse output options after implant using radio frequency communications. While the exemplary system employs fully implanted elements, systems employing partially implanted elements may also be used in accordance with the teachings provided herein.

Referring to FIG. 7, a block diagram of an exemplary stimulation system is shown. IPG 14 contains a signal generation module 1000 and a control module 1010. The control module 1010 is operably coupled to the signal generation module 1000 and instructs signal generation module 1000 regarding the signal to be generated. For example, at any given time or period of time, control module 1010 may instruct signal generation module 1000 to generate an electrical signal having a specified pulse width, frequency, intensity (current or voltage), etc. Control module 1010 may be preprogrammed prior to implantation or receive instructions from programmer 4000 (or another source) through any known or future developed mechanism, such as telemetry. Control module 1010 may include or be operably coupled to memory to store instructions for controlling signal generation module and may contain a processor for controlling which instructions to send to signal generation module 1000 and the timing of the instructions to be sent to signal generation module 1000. Leads 16, 18 are operably coupled to signal generation module 1000 such that a stimulation pulse generated by signal generation module 1000 may be delivered via electrodes 16A, 18A.

While two leads 16, 18 are shown in FIGS. 6-7, it will be understood that any number of one or more leads may be employed. In addition, while FIG. 7 shows two electrodes 16A, 16B, 18A, 18B per lead 16, 18, it will be understood that any number of one or more electrodes per lead may be employed. Stimulation pulses are applied to electrodes 16A and 18A (which typically are cathodes) with respect to a return electrode 16B, 18B (which typically is an anode) to induce a desired area of excitation of electrically excitable tissue in proximity to a source of pain. (A cathode has a more negative potential with respect to an anode, and the electrical current caused by the cathode tends to induce an action potential whereas the electrical current caused by the anode tends to inhibit an action potential.) A return electrode 16B, 18B, such as a ground or other reference electrode, as shown in FIG. 7 is located on same lead 16, 18 as stimulation electrode 16A, 18A. However, it will be understood that a return electrode may be located at nearly any location, whether in proximity to the stimulation electrode 16A, 18A or at a more remote part of the body 15, such as at a metallic case of a pulse generator 14. It will be further understood that any number of one or more return electrodes may be employed. For example, there can be a respective return electrode for each cathode such that a distinct cathode/anode pair is formed for each cathode.

Stimulation Parameters

Various stimulation parameters may be applied to a stimulation signal delivered at one or more electrodes to stimulate or inhibit neurons at one or more locations. Any stimulation parameter may be varied, including frequency and amplitude (current or voltage), pulse width, etc. Various stimulation parameters may be applied at one or more location until therapy is optimized.

Stimulation signals of high and low frequencies can have different therapeutic effects; e.g., high frequency stimulation can reduce primary hyperalgesia (hyperalgesia in the area of injury) and low frequency can reduce secondary hyperalgesia (hyperalgesia outside the area of injury). Also, alternating between high and low frequency stimulation can inhibit development of tolerance to either frequency since different physiological mechanisms are involved.

In addition, low frequency stimulation is likely to stimulate motor neurons, and may cause pulsations in some muscles. This is a benign side effect and is known for both spinal cord stimulation and TENS. In certain circumstances motor stimulation may be desirable. In essence, it may be like applying a massage, which is the basis for much acupuncture that uses electrical stimulation via needles. Accordingly, an example of the use of both low and high frequencies is to apply the low frequency signal/burst to massage muscles and the high frequency signal/burst to suppress pain. The high frequency signal/burst might not be followed by muscle contraction, but it might send pain suppression via muscle or other afferent fibers.

Also, stimulation at low versus high frequency may produce different mechanisms of pain relief and may be useful for treating different types of pain. For example, low frequency TENS has been shown to involve both brain stem and spinal opioid mechanisms and may be useful for treating nociceptive pain. High frequency TENS may be more beneficial for treatment of neuropathic pain. Therapy employing both low and high frequency may be useful for treating mixed pain.

Figure 8:
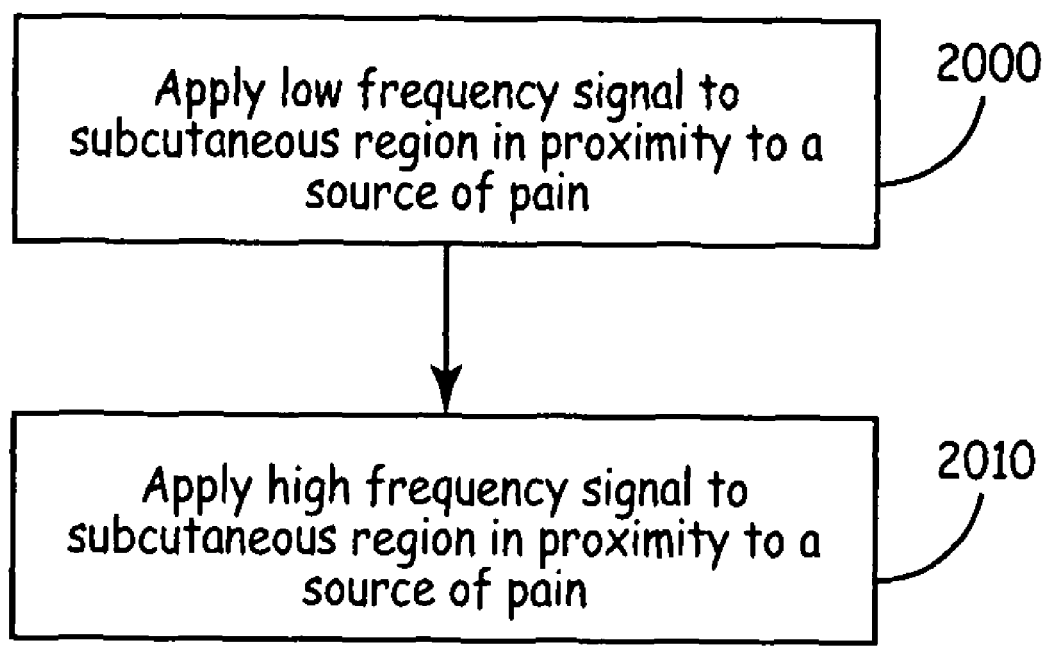
FIG. 8 is a flow diagram of a method employing low and high frequency subcutaneous stimulation.

Referring to FIG. 8, a low frequency stimulation signal may be applied to subcutaneous tissue in proximity to a source of pain 2000 and a high frequency stimulation signal may be applied to subcutaneous tissue in proximity to a source of pain 2010. Stimulation signals at the same one or more electrodes may comprise high frequency and low frequency signals. The high and low frequency signals may be applied at the same (e.g., interlaced) or different times. In an embodiment, high frequency signals are applied at a different set of one or more electrodes than low frequency signals. It will be understood that the different sets of electrodes may contain electrodes in common. Regardless of whether the stimulation electrodes are the same or different, there may be common or separate one or more ground electrodes for the high and low frequency signals.

High frequency signals may be applied at the same time as low frequency signals. High frequency signals may be applied at a different time than low frequency signals. Application of high frequency signals and low frequency signals may be alternated. For example, high frequency signals applied for, e.g., between about one second and about eight hours may be alternated with low frequency signals applied for, e.g., between about one second and about eight hours. The signals may be alternated in a patterned manner or a random manner. The signals may be alternated in response to a sensed signal.

As described herein, delivering high and low frequency signals in short periods could increase therapy effectiveness. Because high and low frequency have different mechanisms, each frequency could be delivered for a short period of time, turned off while the other frequency is delivered, and then restarted before the pain relief has decreased. The two frequencies could also be delivered simultaneously, or interleaved. In another example, if the goal is to stimulate muscle to produce a massage-like effect, the delivery period may be several minutes, e.g. about 1 to about 10 minutes. It may take about 1 minute for the massage to be perceived; after about 10 minutes it may become irritating. In another example, if the intent is to minimize tolerance, the period (specifically the off time) may be on the order of several hours to allow the neurons to return to baseline status after stimulation is turned off.

Duty cycle is the ratio of time spent in delivery of each burst. This can be fixed, e.g., at 3 seconds of high frequency stimulation: 2 seconds low frequency stimulation. Or, alternatively, the duty cycle may vary over time, in a regular manner or irregular, nearly random manner. The length of the bursts may be seconds to minutes long, or may be as short as a small fraction of second, unperceptable to the patient. The pulses in each burst may have different amplitudes or pulse widths. The pulses may be constant current or constant voltage.

Exemplary pulses that may be delivered include alternating bursts of 200 pulses at 80 Hz with 50 pulses at 15 Hz. When using the same cathodes and anodes, an exemplary pulse might include a higher frequency series of pulses, e.g, at 130 Hz and a different amplitude or pulse width or both at 5 Hz.

Electrode Placement

Figure 9:
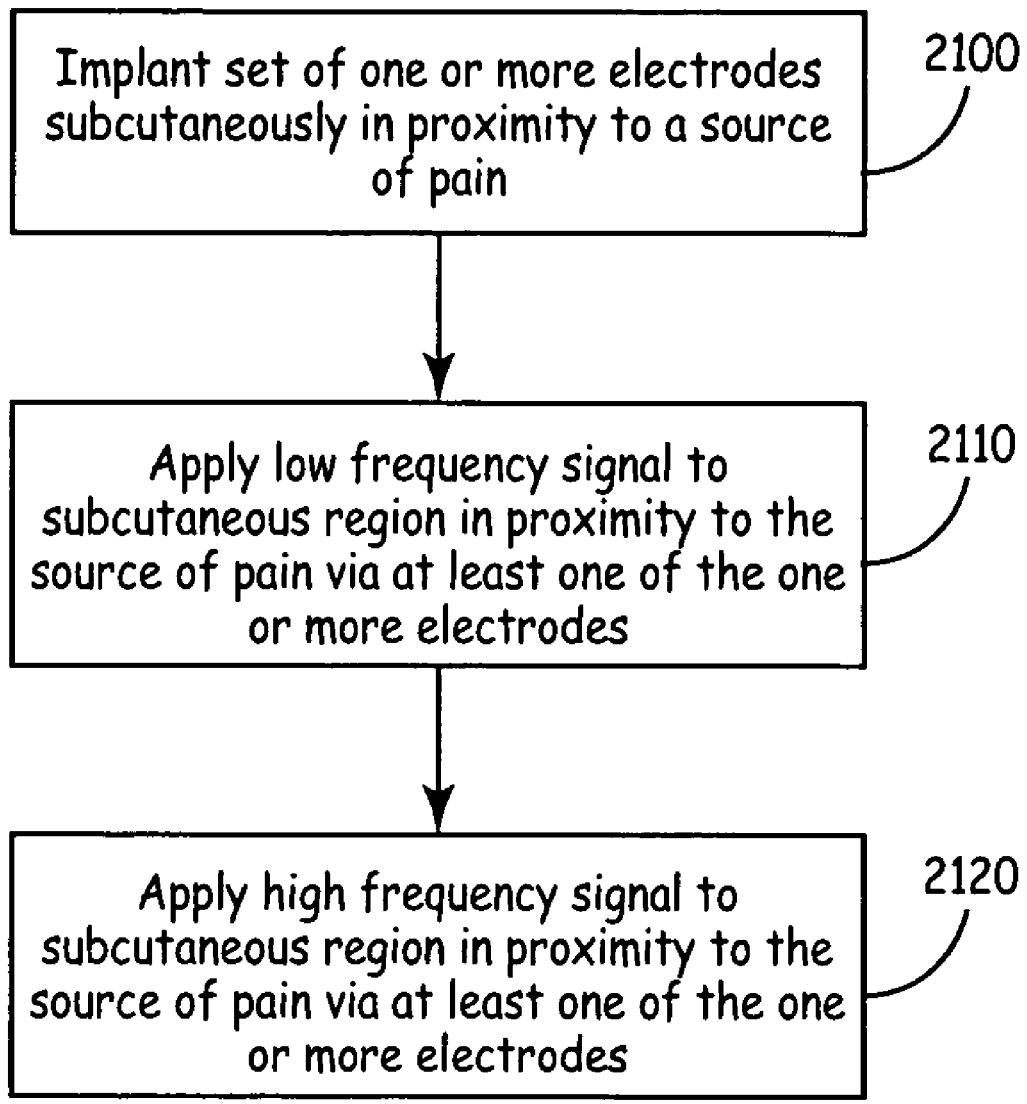
FIG. 9 is a flow diagram of a method employing low and high frequency subcutaneous stimulation.
Figure 10:
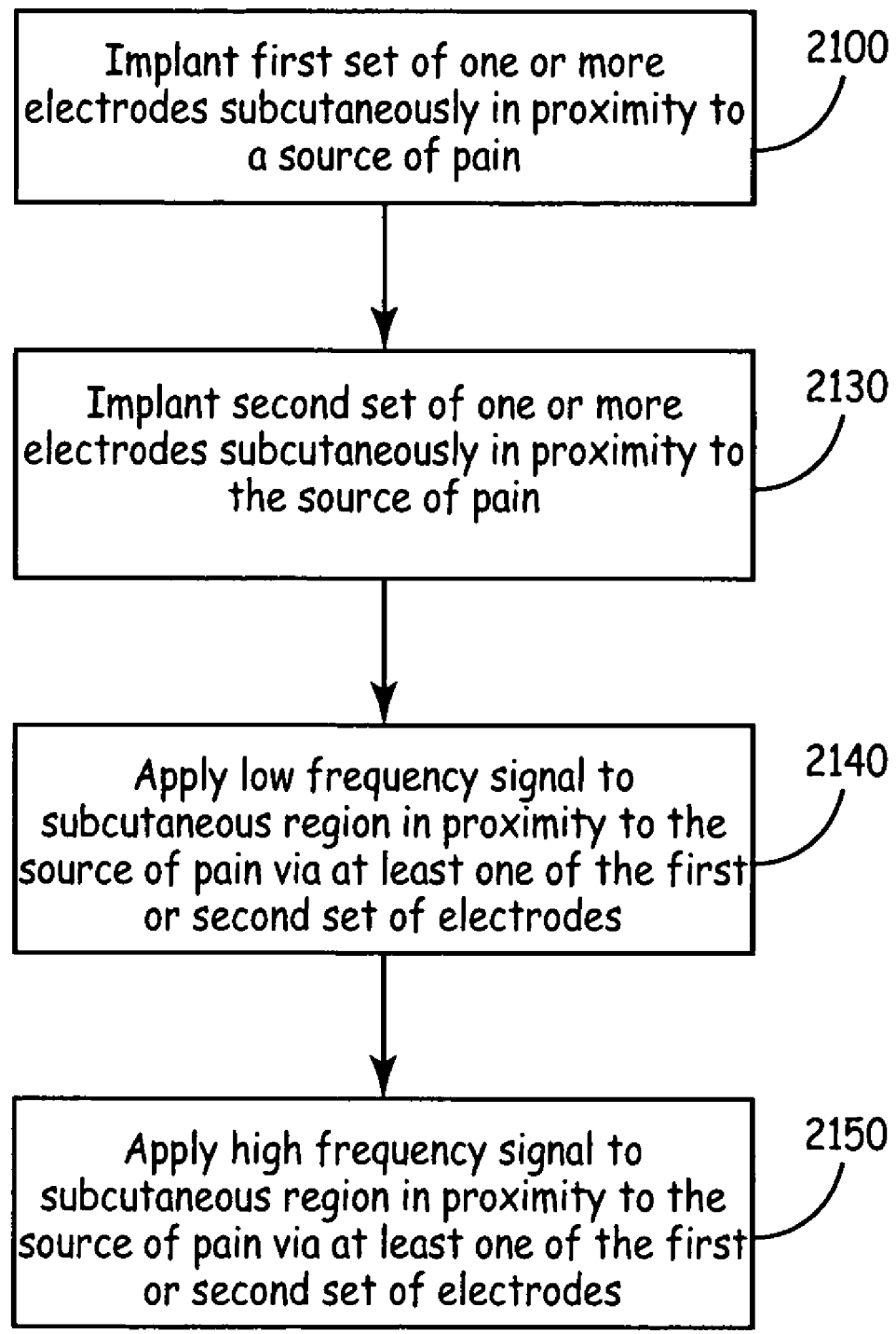
FIG. 10 is a flow diagram of a method employing low and high frequency subcutaneous stimulation.

One or more electrodes may be placed subcutaneously in proximity to a patient's source of pain to deliver a stimulation pulse in accordance with the teachings of the present disclosure. Referring to FIG. 9, at least one set of one or more electrodes is implanted subcutaneously in proximity to a source of pain 2100. A low frequency signal is then applied to the subcutaneous region via at least one of the one or more electrodes 2110 and a high frequency signal is applied to the subcutaneous region via at least one of the one or more electrodes 2120. Alternatively, as shown in FIG. 10, a second set of one or more electrodes (e.g., on a second lead) may be implanted subcutaneously 2130 and the low frequency signal 2140 and high frequency signal 2150 may be applied via at least one of the first or second set of one or more electrodes.

Figure 11:
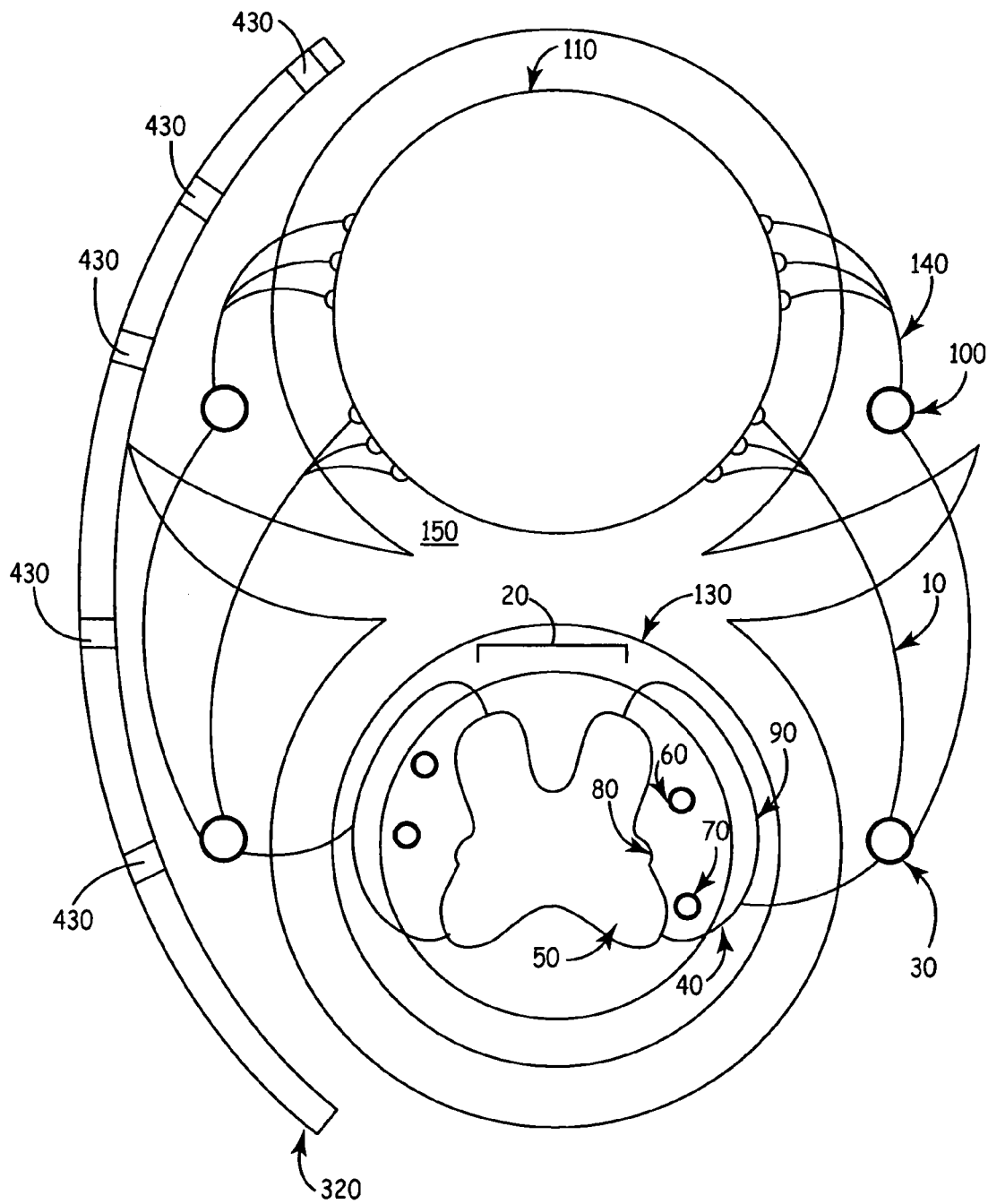
FIG. 11 is a diagrammatic representation of a cross section of a spinal column showing subcutaneous placement of a lead.

Referring to FIG. 11, one example of subcutaneous placement of a lead 320 in proximity to a structure of the back is shown. In FIG. 11, a diagrammatic representation of cross section of vertebrae 150 is shown. The lead 320 may comprise one or more electrodes 430, which may be placed in proximity to, e.g., one or more sympathetic afferent 140 neurons or fibers, one or more sympathetic ganglions 100, or one or more dorsal root ganglions 30. Of course more than one lead 320 may be used to place the one or more electrodes 430 in proximity to the one or more structures. It will be understood that one or more electrodes may also be placed in proximity to discs, facet joints, muscles, ligaments or other structures in proximity to the spinal cord, such that an electrical stimulation signal may be applied to such structures via the electrode(s). In addition, multiple leads 320 may be used to position one or more electrodes 430 over one or more additional vertebral levels. Two, three, four, five, six, seven, or more vertebral levels may be covered in such a manner. Alternatively, a lead 320 may be placed substantially parallel to the spinal cord to allow for electrode placement over more than one vertebral level. In general, subcutaneous placement may serve to provide more specific delivery of a stimulation signal, and thus less potential side effects than TENS and may prove to be more efficient than epidural electrical stimulation for relief of chronic pain. While FIG. 11 shows unilateral placement of lead 320 and electrodes 430, it will be understood that bilateral placement of leads 320 and electrodes 430 is also contemplated and may be desirable.

While FIG. 11 shows an example of subcutaneous lead placement in proximity to structures of the back, it will be understood that the teachings disclosed herein may be applied to other subcutaneous regions of a patient. For example, the lead may be placed subcutaneously in proximity to a patient's knee, elbow, shoulder, leg, etc. to treat pain arising from such peripheral regions. The lead for subcutaneous stimulation may be placed and anchored near a peripheral nerve or ganglion. It may also be placed deliberately farther away, e.g., a centimeter or more, from a given nerve or ganglion, to minimize side effects or recruitment of small fibers that may be nociceptors. It may be placed near muscles, or near nerves innervating muscles, to especially affect muscle afferent or efferent nerves.

In various embodiments, one or more stimulation signal is applied to more than one structure. In an embodiment, at least one of the more than one structures is selected from the group consisting of a sympathetic afferent 140 neuron or fiber and a sympathetic ganglion 100.

Figure 12:
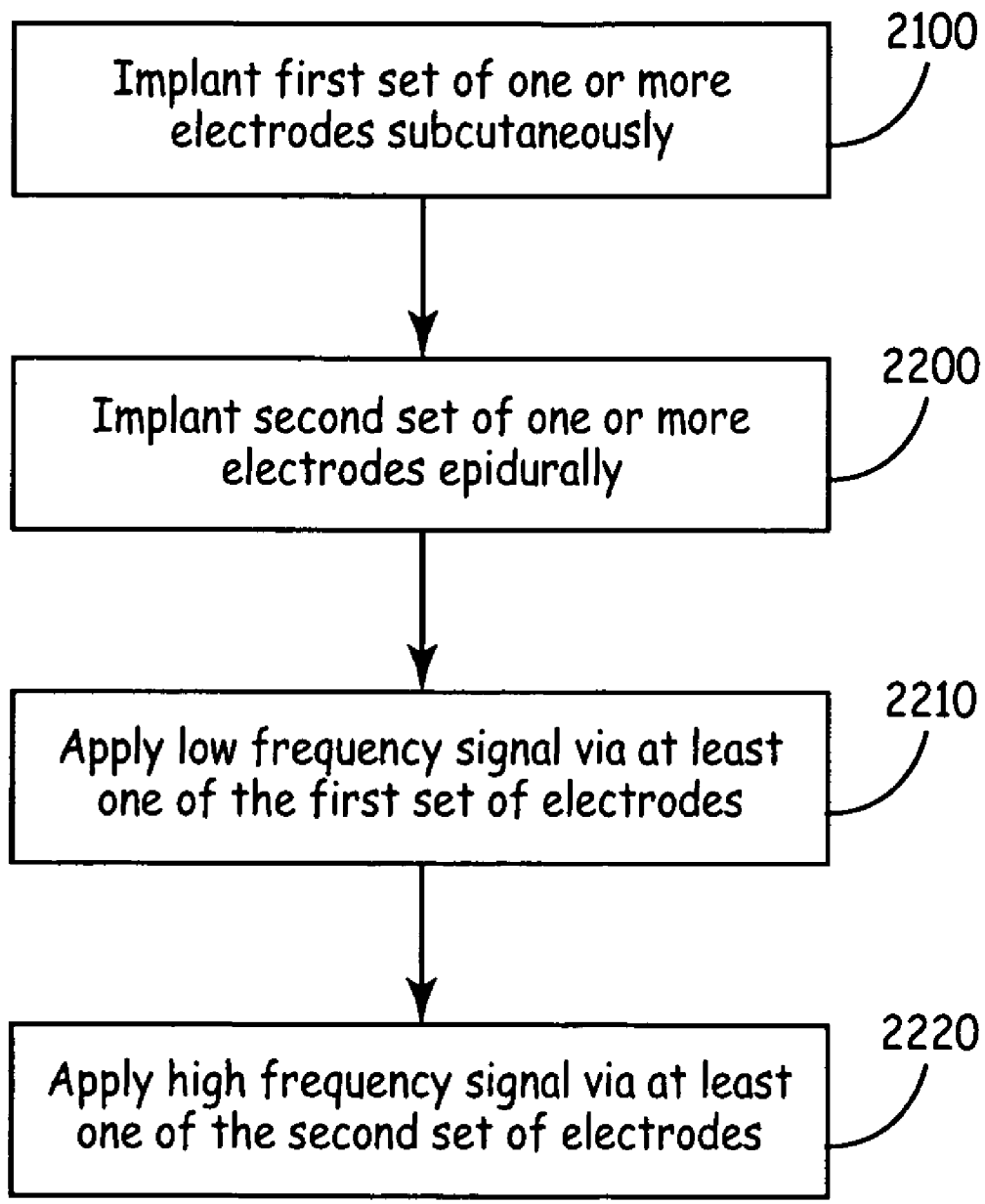
FIG. 12 is a flow diagram of a method employing subcutaneous stimulation and epidural stimulation.

In various embodiments, in addition to the one or more subcutaneously placed electrode, one or more electrode is placed epidurally to deliver a stimulation pulse to the patient's spinal cord. Referring to FIG. 12, a first set of one or more electrodes is implanted subcutaneously 2100, e.g. in proximity to a source of pain, and a second set of one or more electrodes is implanted epidurally 2200. Of course it will be understood that one set of electrodes (e.g, on one lead) may have electrodes implanted subcutaneously and epidurally. Low frequency stimulation is applied to at least one of the first set of one or more electrodes 2210, and high frequency stimulation is applied to at least one of the second set of electrodes 2220. Accordingly, one or more epidurally-placed electrodes may be used to deliver high frequency stimulation, while one or more subcutaneously placed-electrodes may be used to deliver low frequency stimulation (or high frequency stimulation). Of course, one or more epidurally placed electrodes may be used to deliver low frequency stimulation, while one or more subcutaneously placed electrodes may be used to deliver high frequency stimulation (or low frequency stimulation).

Figure 13:
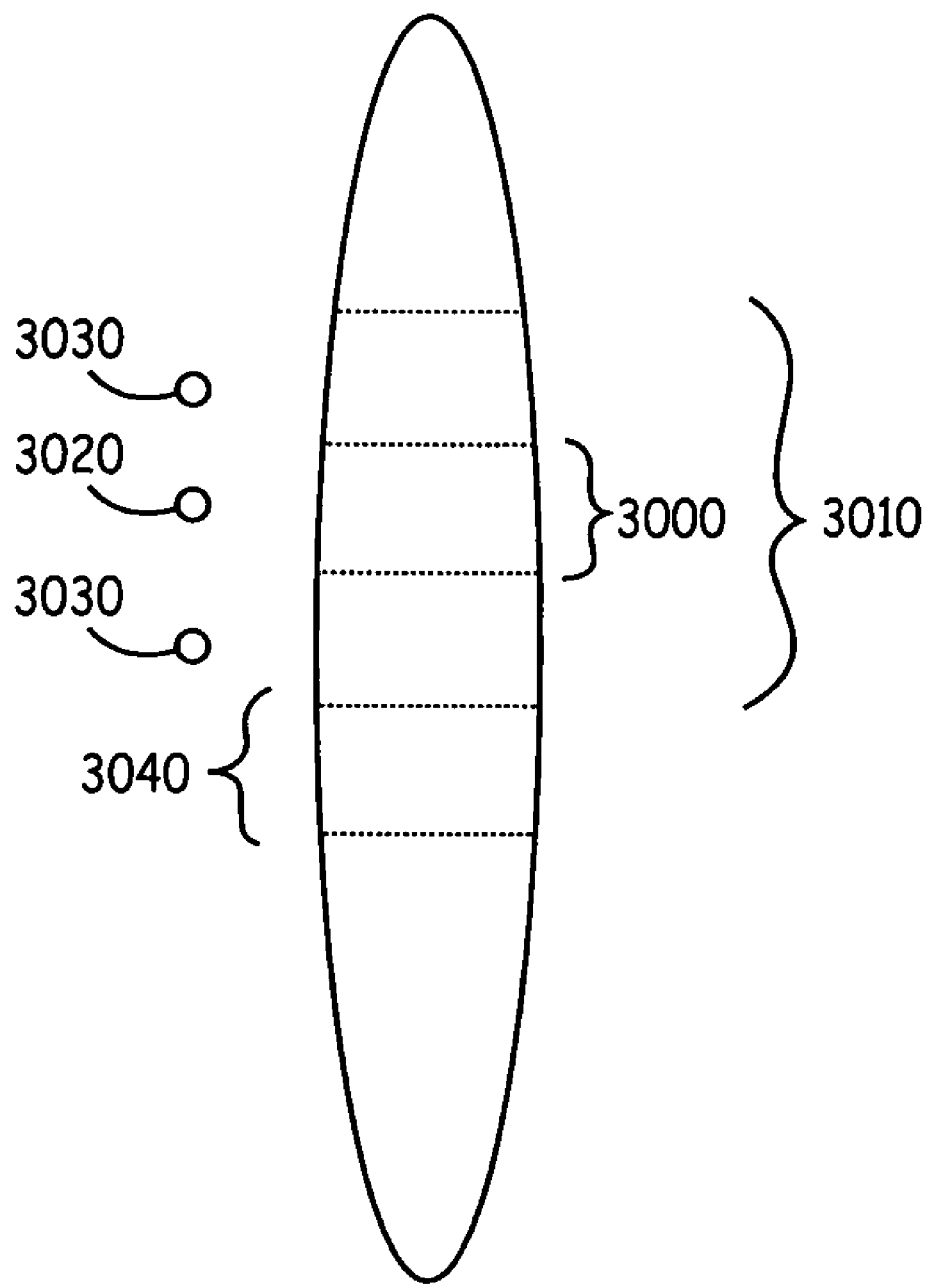
FIG. 13 is a diagrammatic representation of a cross section of a spinal column showing electrodes placed in proximity to a primary hyperalgesic field and a secondary hyperalgesic field.

In an embodiment representatively shown in FIG. 13, one or more electrodes 3020, whether epidurally placed or subcutaneously placed, are placed at a spinal level or in a body region having afferent fibers corresponding to a spinal level at which primary hyperalgesia is sensed 3000 ("primary hyperalgesic field"). One or more electrodes 3030 are placed at a spinal level or in a body region having afferent fibers corresponding to a spinal level at which secondary hyperalgesia is sensed 3010 ("secondary hyperalgesic field"). Of course the primary hyperalgesic field may extend over more than one vertebral level 3040, and it may be desirable to place more than one electrode such that a substantial area in both the primary and secondary hyperalgesic field may directly receive the electrical stimulation signals. In an embodiment, high frequency stimulation is applied via the electrodes placed in proximity to the primary hyperalgesic field and low frequency stimulation is applied via the electrodes placed in proximity to the secondary hyperalgesic field. In certain circumstances, it may be desirable to apply both low and high frequency stimulation to the secondary hyperalgesic field.

Delivery of Pain Treating Agents

Pain treating agents may be administered in any medically acceptably manner, such as orally, parentally, epidurally, or intrathecally. In various embodiments, one or more pain treating agent is administered via an infusion system. Any present or future developed infusion system capable of delivering a pain treating agent to a patient may be used in accordance with the teachings provided herein. The infusion system may include implantable components. One example of a suitable implantable infusion system that may be used in accordance with the teachings presented herein is Medtronic's SynchroMed II infusion device.

Figure 14:
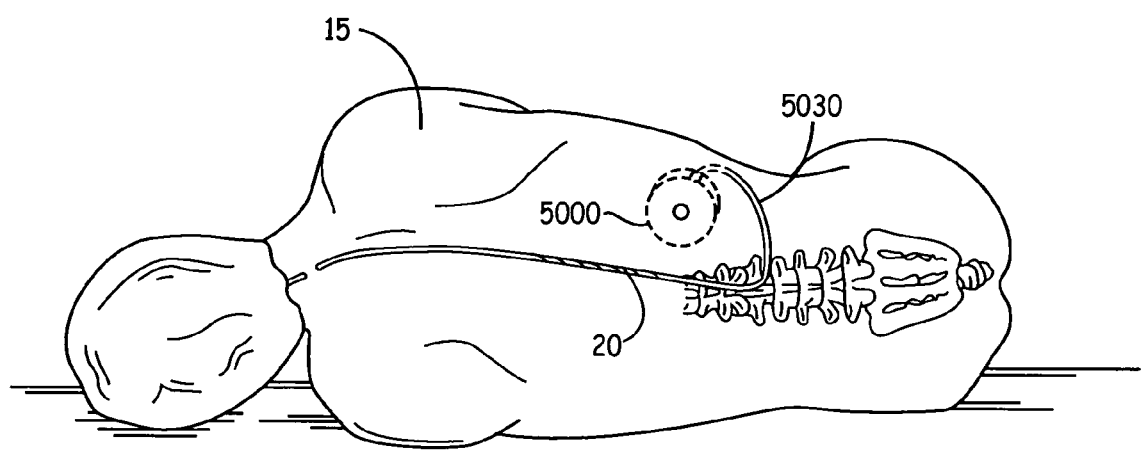
FIG. 14 is a schematic view of an infusion system implanted in a patient.
Figure 15:
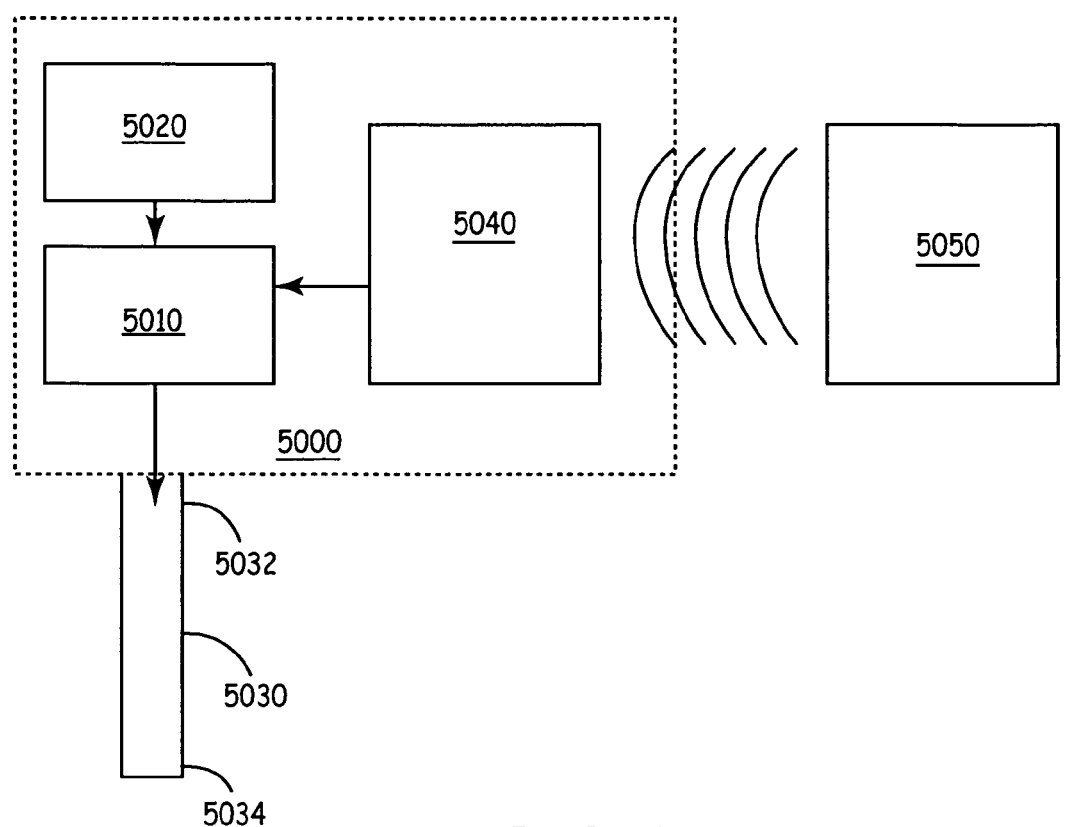
FIG. 15 is a block diagram of an exemplary infusion system.

Referring to FIG. 14, a schematic view of a patient 15 having an implant of an exemplary infusion system useful for delivering a pain treating agent is shown. The exemplary system employs an implantable infusion device 5000. The implantable infusion device 5000 comprises a pump 5010 operable coupled to a reservoir 5020 (see FIG. 15) that may house one or more pain treating agent. The exemplary system includes a catheter 5030 operably coupled to the pump 5010. Catheter 5030, as show in FIG. 14, has a proximal end 5032 and a distal end 5034 adapted to be implanted in a subject. Between (and including) the proximal end 5032 and the distal end 5034, catheter 5030 comprises one or more delivery regions (not shown) through which the pain treating agent may be delivered. The implantable infusion device 5000 may have a port (not shown) into which a hypodermic needle can be inserted to inject a quantity of pain treating agent into reservoir 5020. Infusion device 5000 may have a catheter port (not shown) to which proximal end 5032 of catheter 5030 may be coupled. Infusion device 5000 may be operated to discharge a predetermined dosage of pain treating agent into a target region of a patient 15. As shown in FIG. 15, infusion device 5000 may comprise a control unit 5040 to control the amount of pain treating agent delivered by the infusion device 5000. Control unit 5040 may contain a microprocessor or similar device that can be programmed or deliver instructions to control the amount of therapeutic agent delivered. As shown in FIG. 15, control unit 5040 may be operably coupled to pump 5010 to control output of pain treating agent. Alternatively, control unit 5040 may be operably coupled to one or more valves (not shown) between reservoir 5020 and a delivery portion of catheter 5030 to control flow of pain treating agent, which alternative may be beneficial for infusion devices 5000 lacking a readily controllable pumping mechanism. Control unit 5040 may be in wireless communication (e.g., through telemetry) with an external programmer 5050 or similar control unit. With the use of a programmable device 5000, a controlled amount of pain treating agent may be delivered over a specified time period and different dosage regimens may be programmed for different patients 15. Those skilled in the art will recognize that a programmed infusion device 5000 allows for starting conservatively with lower doses and adjusting to a more aggressive dosing scheme, if warranted, based on safety and efficacy factors.

Figure 16A:
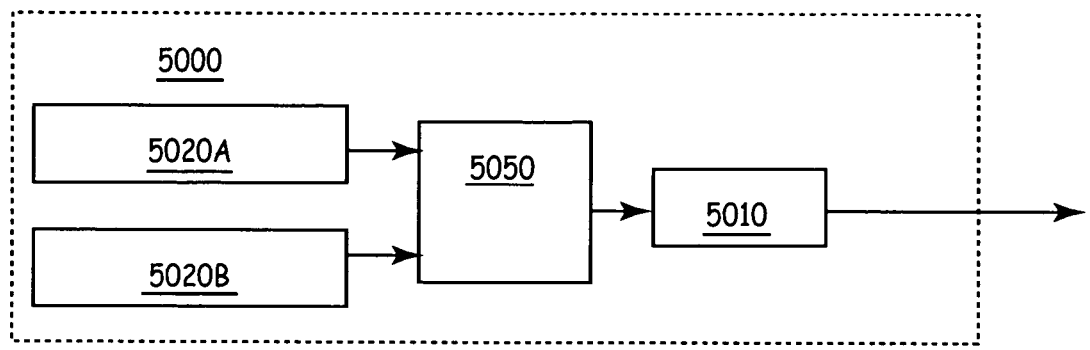
FIGS. 16A-B are a block diagrams of an exemplary implantable infusion systems.
Figure 16B:
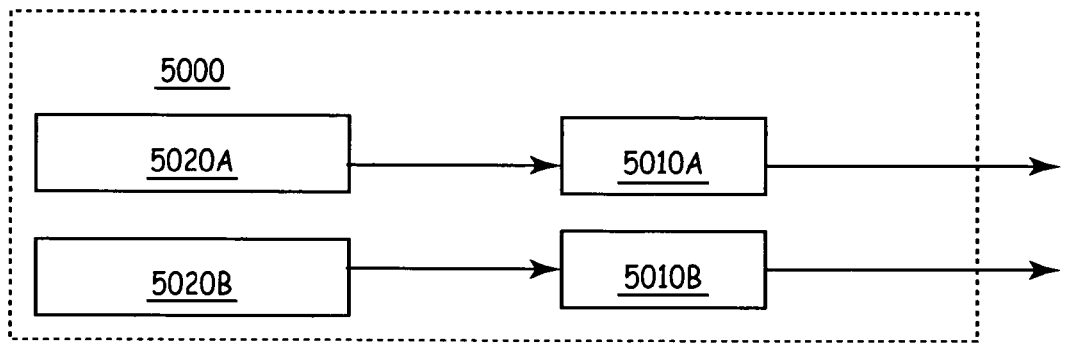

If it is desirable to administer more than one pain treating agent, more than one agent can be mixed into a composition present in the reservoir 5020. The local administration of more than one therapeutic agent can also be accomplished by using more than one infusion device 5000, with the respective reservoirs 5020 of each infusion device 5000 housing a different therapeutic agent. Alternatively and as shown in FIGS. 16A-B, infusion device 5000 may have more than one reservoir 5020, which each reservoir 5020A, 5020B housing additional compositions comprising additional pain treating agents. While only two reservoirs are shown in FIGS. 16A-B, it will be understood that more than two reservoirs may be present.

FIG. 16A shows one example of an infusion device 5000 having more than one reservoir 5020. In FIG. 16A, valve 5050 is disposed between reservoirs 5020A, 5020B and pump 5010 and is operably coupled to reservoirs 5020A, 5020B and pump 5010. Valve 5050 may be operably coupled to and controlled by control unit 5040 (not shown in FIGS. 16A-B) such that pump 5010 may draw from the appropriate reservoir 5020A, 5020B to deliver appropriate therapeutic agent. One or more catheters 5030 may be fluidly coupled to pump 5010 to deliver therapeutic agent to desired locations of the patient 15.

FIG. 16B shows another example of an infusion device 5000 having more than one reservoir 5020A, 5020B. In FIG. 16B each reservoir 5020A, 5020B is coupled to a pump 5010A, 5010B such that each pump 5010A, 5010B may draw fluid from a reservoir 5020A, 5020B housing a different pain treating agent. One or more catheters 5030 may be fluidly coupled to pump 5010A, 5010B to deliver therapeutic agent to desired locations of the patient 15. If only one catheter (not shown) is operably coupled to pumps 5010A, 5010B, a valve (not shown) or similar device may be employed between pump 5010A, 5010B and catheter (not shown in FIG. 16B).

According to various embodiments of the invention, a pain treating agent is administered intrathecally to a patient 15. FIG. 14 illustrates a system adapted for intrathecal delivery of a pain treating agent. As shown in FIG. 14, an infusion system or device 5000 may be implanted below the skin of a patient 15. Preferably the infusion device 5000 is implanted in a location where the implantation interferes as little as practicable with patient activity. One suitable location for implanting the infusion device 5000 is subcutaneously in the lower abdomen. For intrathecal delivery, catheter 5030 may be positioned so that the distal end (not shown in FIG. 14) is located in the subarachnoid space of the spinal cord such that a delivery region (not shown) of catheter is also located within the subarachnoid space. It will be understood that the delivery region can be placed in a multitude of locations to direct delivery of a therapeutic agent to a multitude of locations within the cerebrospinal fluid of the patient 15. The location of the distal end (not shown) and delivery region(s) of the catheter 5030 may be adjusted to improve therapeutic efficacy. While not shown, it will be understood that infusion devices or systems 5000 may be used to deliver therapeutic agent to subcutaneous or other locations in proximity to spinal structures, in proximity to a source of pain, or practically any other location of the body to which a delivery region of a catheter 5030 may be placed.

Pain Treating Agents

Pain treating agents may be administered in addition to application of stimulation therapy as described hereinabove. Pain treating agents may be administered at any time relative stimulation therapy. For example, pain treating agents may be administered throughout stimulation therapy, may overlap with one or more portions of stimulation therapy, may alternate with stimulation therapy, or may be coordinated to be delivered at a predetermined time relative to stimulation therapy.

Any medically acceptable pain treating agent may be administered according to the teachings provided herein. Non-limiting examples of pain treating agents include analgesics, anesthetics, and anti-inflammatory agents. Pain treating agents may be administered locally or systemically and may be administered to one or more locations or by one or more routes. For example, a pain treating agent may be administered intrathecally or subcutaneously, e.g. in proximity to the spinal cord or in proximity to a site of pain.

Pain treating agents for which it may be beneficial to administer in proximity to a site of pain include anti-inflammatory agents such as steroids, NSAIDS, TNF-alpha inhibitors (soluble receptors, antibodies, etc.), local anesthetics, and NMDA antagonists (ketamine, etc.). For back pain, such as chronic low back pain, a pain treating agent may be delivered to cover spinal discs, the sympathetic chain, nerve roots, sympathetic ganglia, etc. The pain treating agent may be delivered such that it provides bilateral and multi-segmental coverage.

Some exemplary pain treating agents that may be suitable for supraspinal (e.g., intracerebroventricular or intraparenchymal), intrathecal or epidural delivery include opioid agonists, alpha2 adrenergic agonists (clonidine ($\alpha_{2a}$), moxonidine ($\alpha_{2c}$), etc.), serotonin agonists and reuptake inhibitors, adenosine agonists, and the like. Agents, such as opioid agonists, may be delivered to both the brain and the spine to produce synergistic effects. To achieve supraspinal administration, pain treating agents may be delivered into the intrathecal space and move through cerebrospinal fluid into the brain (as described in, e.g., U.S. patent application Ser. No. 10/745,731, entitled "Method of delivering drug to the brain via the spinal canal," filed Dec. 23, 2003).

For pain treating agents that are to be administered intrathecally or otherwise injected or infused, the agents may be formulated into injectable compositions. Injectable compositions include solutions, suspensions, and the like. Injectable solutions or suspensions may be formulated according to techniques well-known in the art (see, for example, Remington's Pharmaceutical Sciences, Chapter 43, 14th Ed., Mack Publishing Co., Easton, Pa.), using suitable dispersing or wetting and suspending agents, such as sterile oils, including synthetic mono- or diglycerides, and fatty acids, including oleic acid.

Solutions or suspensions comprising a pain treating agent may be prepared in water, saline, isotonic saline, phosphate-buffered saline, and the like and may optionally be mixed with a nontoxic surfactant. Dispersions may also be prepared in glycerol, liquid polyethylene, glycols, DNA, vegetable oils, triacetin, and the like and mixtures thereof. Under ordinary conditions of storage and use, these preparations may contain a preservative to prevent the growth of microorganisms. Pharmaceutical dosage forms suitable for injection or infusion include sterile, aqueous solutions or dispersions or sterile powders comprising an active ingredient in which powders are adapted for the extemporaneous preparation of sterile injectable or infusible solutions or dispersions. Preferably, the ultimate dosage form is a sterile fluid and stable under the conditions of manufacture and storage. A liquid carrier or vehicle of the solution, suspension or dispersion may be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. Proper fluidity of solutions, suspensions or dispersions may be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin. Excipients that increase solubility, such as cyclodextrin, may be added.

Sterile injectable compositions may be prepared by incorporating a pain treating agent in the required amount in the appropriate solvent with various other ingredients as enumerated above and, as required, followed by sterilization. Any means for sterilization may be used. For example, the injectable composition may be autoclaved or filter sterilized. In the case of sterile powders for the preparation of sterile injectable solutions, the preferred methods of preparation are vacuum drying and freeze-drying techniques, which yield a powder of the active ingredient plus any additional desired ingredient present in a previously sterile-filtered solutions. Injectable compositions may be heat treated or sterilized by autoclaving.

Pain treating agents may be present in compositions at any acceptable concentration. Non-limiting examples of concentrations of pain treating agents are shown in the following table for exemplary purposes:

TABLE 1

Exemplary suitable concentration ranges for exemplary pain treating agents

| Pain Treating Agent | Concentration (mg/ml) |
|---|---|
| Morphine | 10-50 |
| Hydromorphone | 1-50 |
| Bupivacaine | 2.5-25 |
| Clonidine | 0.05-10 |
| Ketamine | 0.5-100 |

Pain treating agents may be administered at any acceptable dosage. Non-limiting examples of daily dosages of pain treating agents administered intrathecally are shown in the following table for exemplary purposes:

TABLE 2

Exemplary suitable dosage ranges for exemplary pain treating agents

| Pain Treating Agent | Daily Dose |
|---|---|
| Morphine | 1-5 mg* |
| Hydromorphone | 1-15 mg |
| Fentanyl | 10-150 µg |
| Methadone | 5-60 mg |
| Merperidine | 30-60 mg |
| Bupivacaine | 2.5-25 mg |
| Ropivacaine | 10-150 mg |
| Clonidine | 10-1200 µg |
| Ketamine | 40-50 mg |

*For purposes of example, 1-5 mg/day of morphine intrathecal corresponds roughly to 75-375 mg/day oral It will be understood that the use of combination therapy may provide for increased efficacy while allowing for use of lower doses of each agent in the combination therapy (relative to if any agent were used alone in monotherapy). Decreased doses of each individual agent in combination therapy may limit side effects associated with any one of the individual agents. For example, combination therapy with clonidine and morphine may allow for a decreased dose of morphine. By decreasing morphine exposure, tolerance and dose escalation of the morphine can be reduced. In certain circumstances, it may be desirable to initiate therapy with a combination therapy rather than with monotherapy. For example, initiating combination therapy, instead of adding a second pain treating agent to an ongoing therapy in which significant tolerance has already developed, may be desirable.

Coordinated Stimulation and Infusion for Treating Pain

Pain treating agents, whether alone or in combination, may be administered in combination with stimulation. In various embodiments, pain treating agents may be administered during periods of high or low frequency stimulation. Preferably, a drug having a synergistic effect with either high or low frequency stimulation is administered at the appropriate time. For example, a µ-opioid agonist, such as morphine, is administered during a period of low frequency stimulation or a δ-opioid agonist, such as dynorphin or SNC-80, or an α2 adrenergic agonist, such as clonidine, is administered during a period of high frequency stimulation. Of course it will be understood that the timing of the administration of the pain treating agent may be adjusted such that the pain treating agent is present at a desired body location at a time when either the low or high frequency stimulation is delivered. Accordingly, the pain treating agent may be administered at a predetermined time relative to the low or high frequency stimulation to allow for the drug to diffuse to a body location where an enhanced paint treating effect may be experienced by the patient in combination with the stimulation. The time for a pain treating agent to reach a desired location will be known to one skilled in the administration of such agents. By way of example, intrathecal administration of morphine may take from about 30 minutes to about 120 minutes to reach intended spinal receptors in sufficient concentration to produce a clinical effect. If it is desirable to have an agent act in the brain via intrathecal administration, it may be take about one additional hour for the agent to reach the brain. For example, if it is desired to have morphine present in the patient's brain at a time when low frequency stimulation is applied, it may be desirable to administer morphine intrathecally about 90 minutes to about 180 minutes prior to delivering the low frequency stimulation.

Figure 17A:
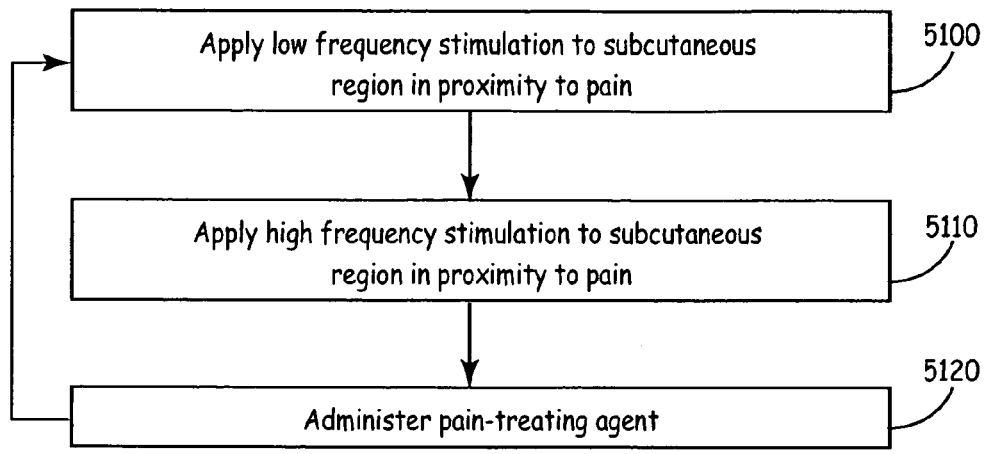
FIGS. 17A-C are flow diagrams of administration of a pain treating agent in conjunction with application of stimulation therapy.
Figure 17B:
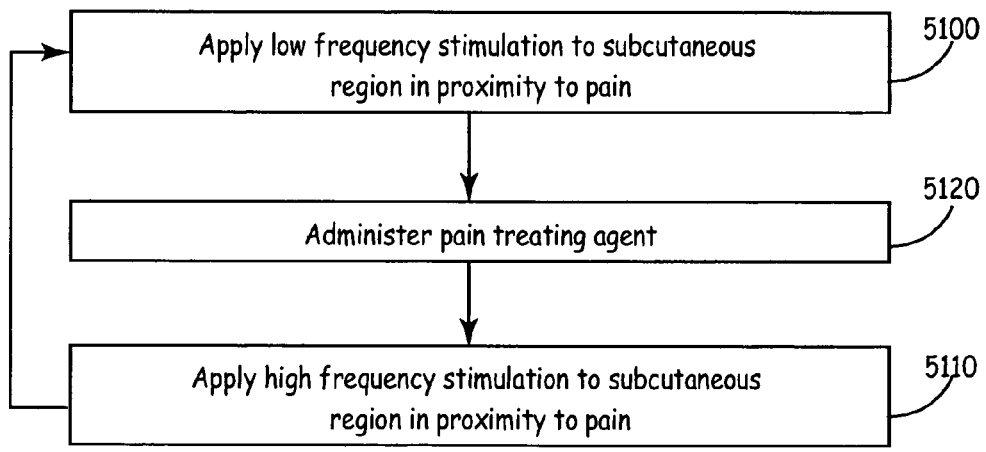
Figure 17C:
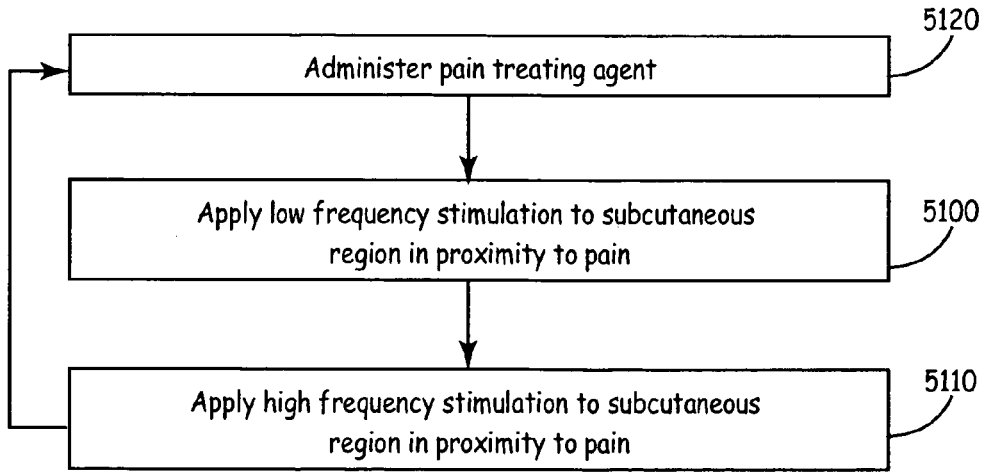
Figure 18A:
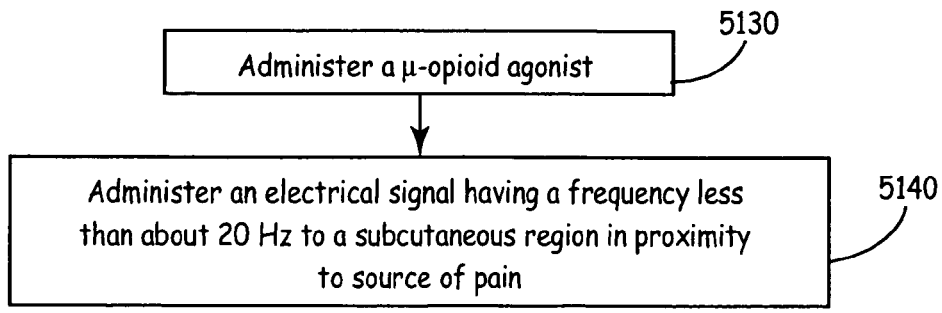
FIGS. 18A-D are flow diagrams of administration of a pain treating agent in conjunction with application of stimulation therapy.
Figure 18B:
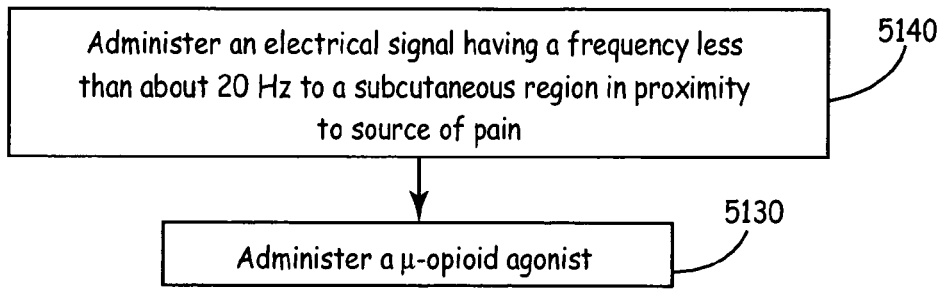
Figure 18C:
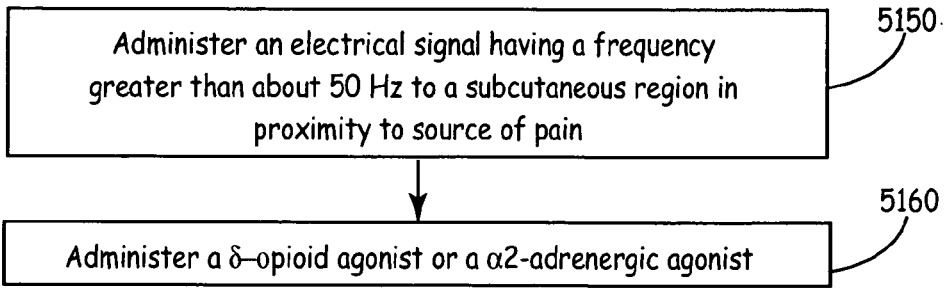
Figure 18D:
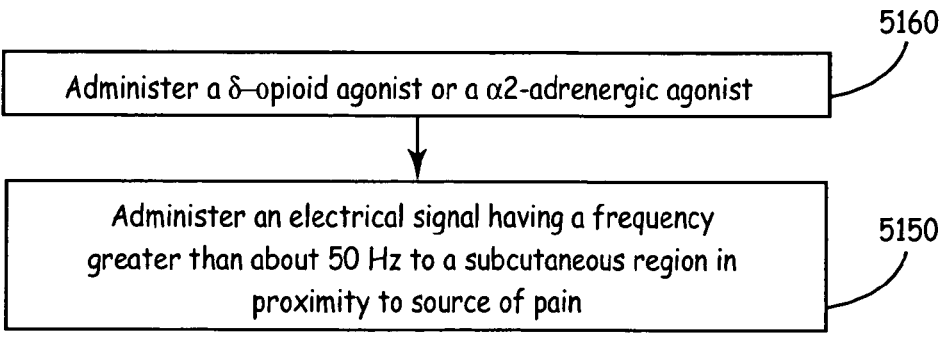
Figure 19:
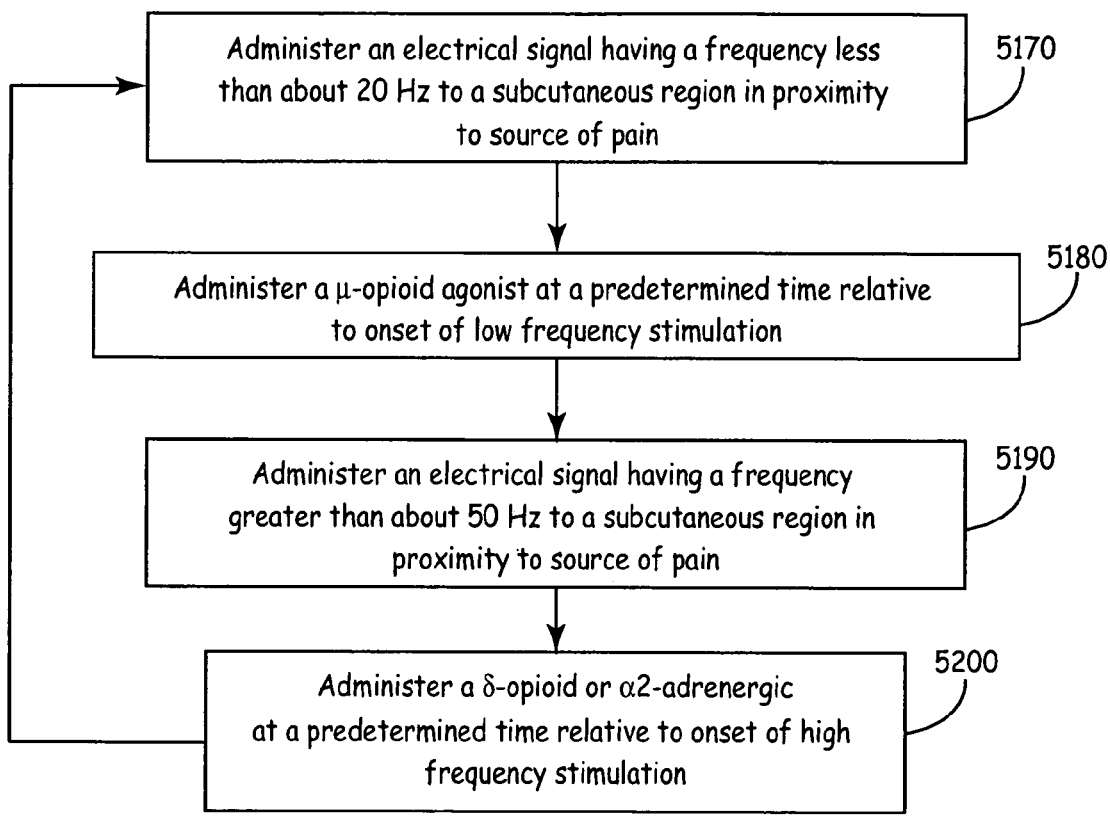
FIG. 19 is a flow diagram of administration of a pain treating agent in conjunction with application of stimulation therapy.

Examples of how pain treating agents may be administered in conjunction with stimulation therapy are shown in FIGS. 17-19. As shown in FIG. 17A, pain treating agent may be administered (5120) following application of low frequency stimulation (5100) and high frequency stimulation (5110). FIG. 17B shows a pain treating agent may be administered (5120) between application of low frequency stimulation (5100) and high frequency stimulation (5130), and FIG. 17C shows a pain treating agent may be administered (5120) prior to application of low frequency stimulation (5100) and high frequency stimulation (5130). Regardless of when, in relation to application of stimulation, a pain treating agent is administered, the application of a pain treating agent may be administered in a cyclic fashion relative to application of stimulation as shown in FIGS. 17A-C. Such cyclic administration of pain treating agents and high and low frequency stimulation may reduce tolerance to any one or more of the therapies (i.e., administration of a pain treating agent 5120, application of low frequency stimulation 5100, and application of high frequency stimulation 5110). Of course, the pain treating agent may be administered at the same time as either high or low frequency stimulation to produce enhanced pain relief.

As shown in FIGS. 18A-D, a pain treating agent whose effect may be potentiated by concurrent administration of either low or high frequency stimulation may be administered in conjunction with either low or high frequency stimulation. As shown in FIGS. 18A-B, a µ-opioid agonist may be administered in conjunction with low frequency stimulation. It will be understood that agents other than µ-opioid agonists that could be beneficially combined with low frequency stimulation may also be administered in conjunction with low frequency stimulation. A µ-opioid agonist may be administered (5130) prior to beginning application of low frequency stimulation to a subcutaneous region in proximity to a source of pain (5140), as shown in FIG. 18A. This may allow the µ-opioid agonist time to diffuse to its location of action so that when the low frequency stimulation is applied, the pain treating effects may be cumulative (or preferably more than cumulative). Alternatively, as shown in FIG. 18B a µ-opioid agonist may be administered (5130) following the onset of application of low frequency stimulation to a subcutaneous region in proximity to a source of pain (5140). This may allow sufficient time for cellular responses to the stimulation to be optimized so that the effects of the stimulation and the administration of the pain treating agent can be cumulative (or preferably more than cumulative). Of course, the onset of administration of the pain treating agent and the onset of low frequency stimulation may occur at substantially the same time. FIG. 18C-D, show that a pain treating agent (e.g., a δ-opioid agonist or an α2-adrenergic agonist) may be administered (5160) in conjunction with high frequency stimulation (5150) in a manner similar to that described above with regard to a µ-opioid agonist and low frequency stimulation (FIGS. 18A-B). While not shown in FIG. 18, it will be understood that a pain treating agent may be administered in conjunction with spinal cord stimulation.

Referring to FIG. 19, an example of how a first pain treating agent may be administered in conjunction with low frequency stimulation and how a second pain treating agent may be administered in conjunction with high frequency stimulation is shown. As shown in FIG. 19, a µ-opioid agonist may be administered (5180) in conjunction with low frequency stimulation applied subcutaneously to a region in proximity to a source of pain (5170) and a δ-opioid agonist or an $\alpha_2$-adrenergic agonist may be administered (5200) in conjunction with high frequency stimulation applied subcutaneously to a region in proximity to a source of pain (5190). As shown in FIG. 19, the administration of pain treating agents and stimulation signals may occur in a cyclic fashion as follows: (i) administration of low frequency stimulation (5170), (ii) administration of µ-opioid agonist (5180), (iii) administration of high frequency stimulation (5190), (iv) administration of δ-opioid agonist or an $\alpha_2$-adrenergic agonist (5200), (v) repeat at (i). Another example of how administration of pain treating agents and stimulation signals may occur in a cyclic fashion is: (i) administration of p-opioid agonist (5180), (ii) administration of low frequency stimulation, (iii) administration of δ-opioid agonist or an $\alpha_2$-adrenergic agonist (5200), (iv) administration of high frequency stimulation (5190), (v) repeat at (i). Of course the order of administration of each individual component may be modified and the onset of the administration of the pain treating agent and the onset of the high or low frequency stimulation may occur at substantially the same time. The administration in such a cyclic manner may reduce the tolerance that may develop to any given therapy (i.e., δ-opioid agonist, low frequency stimulation, p-opioid agonist or $\alpha_2$-adrenergic agonist, and high frequency stimulation). While not shown in FIG. 19, it will be understood that a pain treating agent may be administered in conjunction with spinal cord stimulation.

While the discussion with regard to FIGS. 17-19 refers to delivery of a pain treating agent based on the status of stimulation therapy, it will be understood that stimulation therapy may be applied based on the status of pain treating agent delivery.

Further it will be understood that it may not always be desirable to administer (i) a δ-opioid agonist and high frequency stimulation concurrently or (ii) µ-opioid agonist and low frequency stimulation concurrently because cross-tolerance may develop. To reduce tolerance it may be desirable to cycle between (i) high and low frequency stimulation and (ii) delivery of a δ-opioid agonist and a µ-opioid agonist, (a) high frequency stimulation and delivery of a µ-opioid agonist and (b) low frequency stimulation and delivery of a δ-opioid agonist, etc. The cycling period could be seconds, minutes, hours, days, weeks, or months.

Systems for Coordinated Delivery of Stimulation and Infusion Therapy

In various embodiments, the invention provides systems capable of delivering coordinated stimulation therapy and infusion therapy. A stimulation signal may be delivered at a predetermined time relative to infusion of, e.g., a particular type of therapeutic agent, such as a pain treating agent, or a therapeutic agent at a particular rate, etc. Of course, infusion of a therapeutic agent may be timed relative to application of a particular stimulation signal.

Figure 20A:
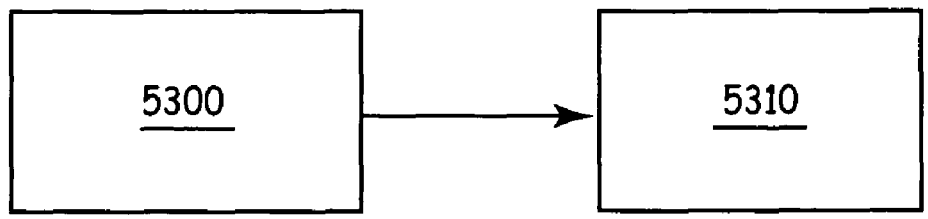
FIGS. 20A-C are block diagrams showing communication between systems comprising a stimulation module and an infusion module.
Figure 20B:
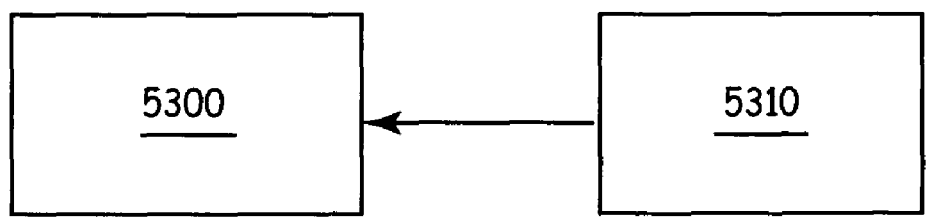
Figure 20C:
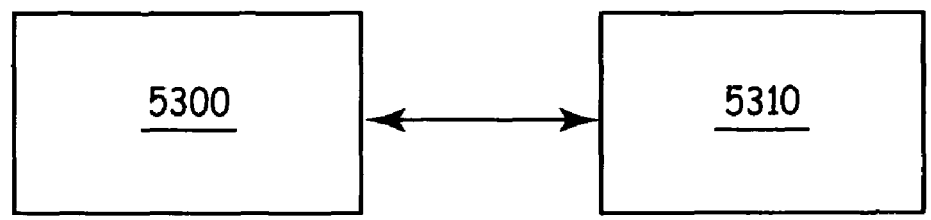

Referring to FIG. 20, the coordinated delivery of a stimulation therapy and an infusion therapy may involve communication between a stimulation module 5300 and an infusion module 5310. The stimulation module 5300 and the infusion module 5310 may be housed in a single housing or may be part of separate devices, such as an implantable pulse generator 14 or an implantable infusion device 5000. As shown in FIG. 20A, the infusion module 5310 may receive information regarding the status of the stimulation module 5300, such as whether the stimulation module 5300 is producing a stimulation signal that may trigger a change in infusion parameters in the infusion module 5310. Similarly and as shown in FIG. 20B, the stimulation module 5300 may receive information regarding the status of the infusion module 5310, such as whether the infusion module 5310 is infusing an agent at a rate that may trigger a change in infusion parameters in the stimulation module 5300. Of course the information may be bi-directional as shown in FIG. 20C; i.e., the infusion module 5310 may receive information regarding the status of the stimulation module 5300 and the stimulation module 5300 may receive information regarding the status of the infusion module 5310. Of course, there may be more than one infusion module 5310 and more than one stimulation module 5300 and communication may be coordinated between the various infusion modules 5310 and stimulation modules 5300 so that stimulation at the particular parameters is applied to a particular body location at an appropriate time relative to infusion with particular parameters at a particular body location. The communication between a stimulation module 5300 and an infusion module 5310 may occur wirelessly or through wires. If a stimulation module 5300 and an infusion module 5310 are housed in separate devices, it may be desirable for communication to occur wirelessly, e.g. through telemetry. If a stimulation module 5300 and an infusion module 5310 are housed in a single device, it may be desirable for control of communication to occur through a processor (not shown) also housed within the device.

Figure 21A:
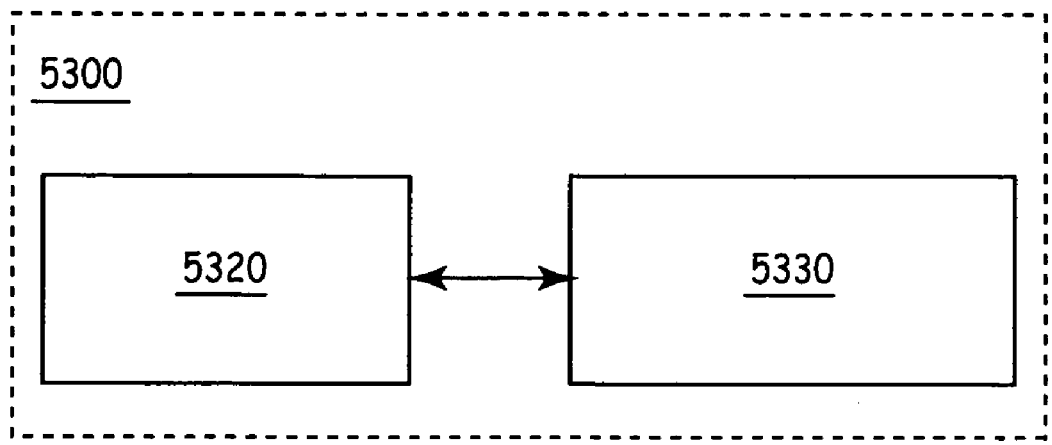
FIGS. 21A-B are block diagrams of an exemplary stimulation module and infusion model, respectively.
Figure 21B:
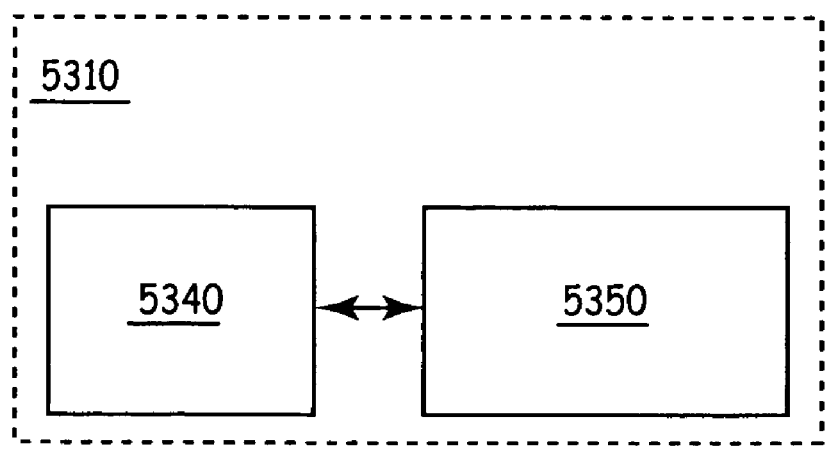

Referring to FIGS. 21A-B, stimulation module 5300 may include a pulse generation module 5320 and a stimulation control module 5330. Infusion module 5310 may include a pump module 5340 and a pump control module 5350. Stimulation control module 5330 may receive information regarding the status of infusion module 5310 and may control parameters of a stimulation signal to be delivered. Similarly, pump control module 5350 may receive information regarding the status of stimulation module 5300 and may control parameters associated with infusion of a therapeutic agent.

Figure 22:
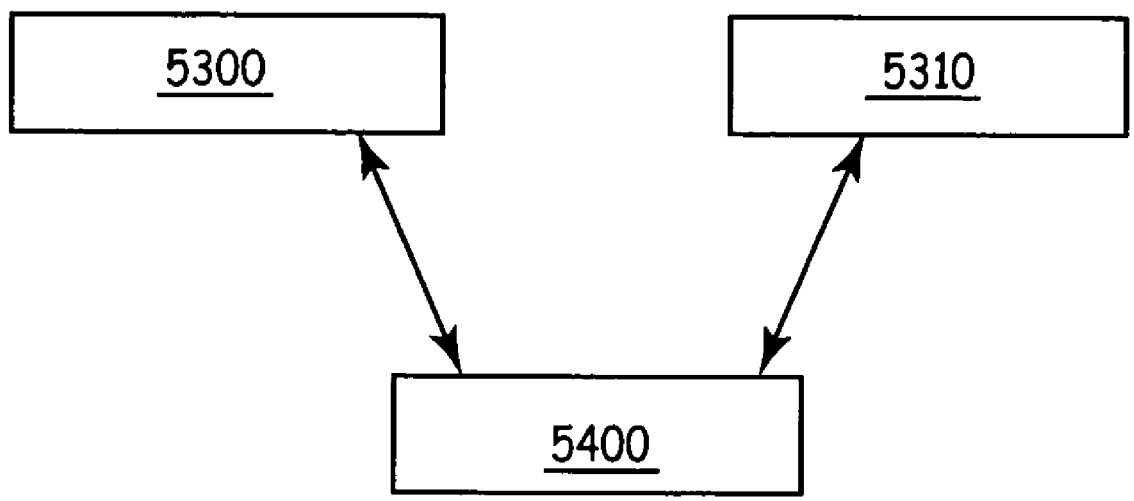
FIG. 22 is a block diagram showing communication between systems comprising a stimulation module, an infusion module and a control unit.

Referring to FIG. 22, a control unit 5400 separate from stimulation module 5300 and infusion module 5310 may coordinate communication between stimulation module 5300 and infusion module 5310. While communication is shown as bidirectional in FIG. 22, it will be understood that communication may be unidirectional between control unit 5400 and stimulation module 5300 and infusion module 5310. For example, control unit 5400 may receive information regarding the status of stimulation module 5300 and may transmit such information to pump control module 5350 of infusion module 5310. It will be understood that infusion module 5310 and stimulation module 5300 may communicate directly with each other.

Figure 23A:
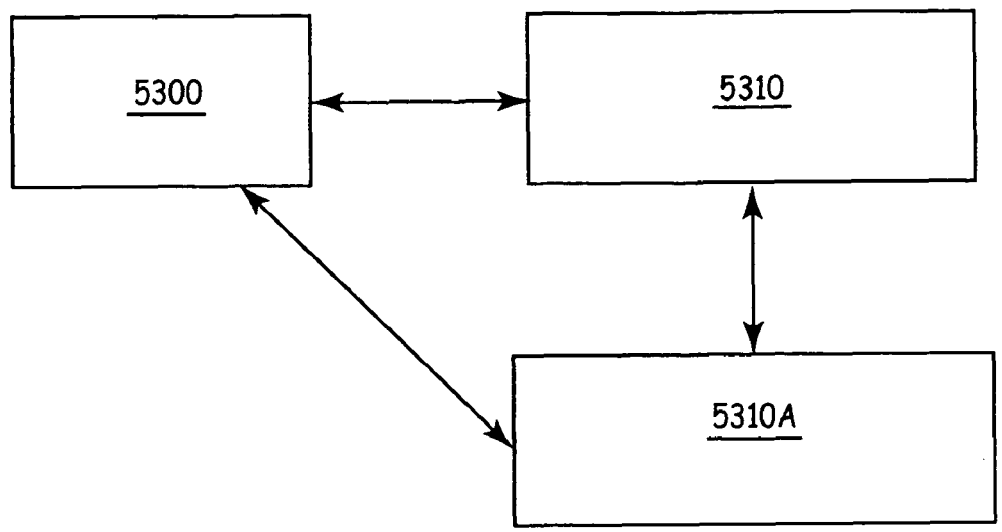
FIGS. 23A-B are block diagrams showing communication between systems comprising a stimulation module and two infusion modules.
Figure 23B:
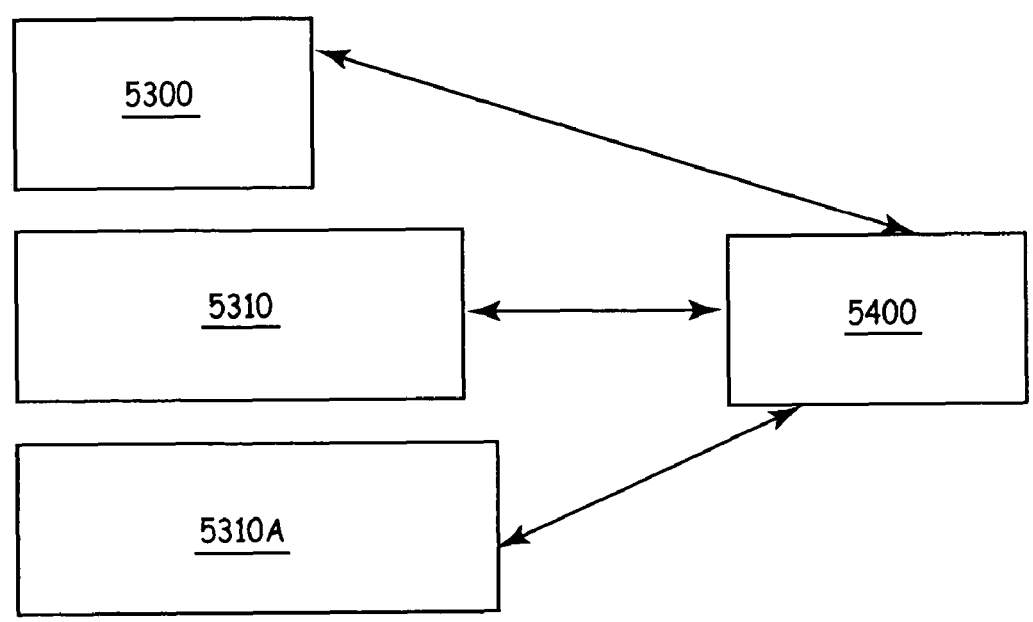

Referring to FIGS. 23A-B, exemplary systems employing two infusion modules 5310, 5310A and one stimulation module 5300 are shown. Such systems may be configured such that a first infusion module 5310 delivers a first therapeutic agent and a second infusion module 5310A delivers a second therapeutic agent. The timing of delivery of the first and second therapeutic agents may be controlled relative to delivery of a particular stimulation signal generated by stimulation module 5300 by communication between stimulation module and first and second infusion modules 5310, 5310A. First infusion module 5310 and second infusion module 5310A may be configured to communicate with each other in various embodiments. As shown in FIG. 23B, a separate control unit 5400 may be employed to coordinate the timing of delivery of a first therapeutic agent from first infusion module 5310, a second therapeutic agent from second infusion module 5310A, and a stimulation signal from stimulation module 5300.

Systems employing a stimulation module 5300 and two infusion modules 5310, 5310A or an infusion module 5310 having multiple reservoirs 5020 may be configured for treating pain. For example: first infusion module 5310 may contain a reservoir 5020 housing a first pain treating agent; second infusion module 5310A may contain a reservoir housing a second pain treating agent; and stimulation module 5300 may contain a pulse generation module 5320 capable of generating a high frequency electrical signal and a low frequency electrical signal. The first pain treating agent may be delivered to a location in the patient 15 at a predetermined time relative to the application of low or high frequency signals, and the second pain treating agent may be delivered to a location in the patient 15 at a predetermined time relative to the application of low or high frequency signals, as described hereinabove.

Figure 24A:
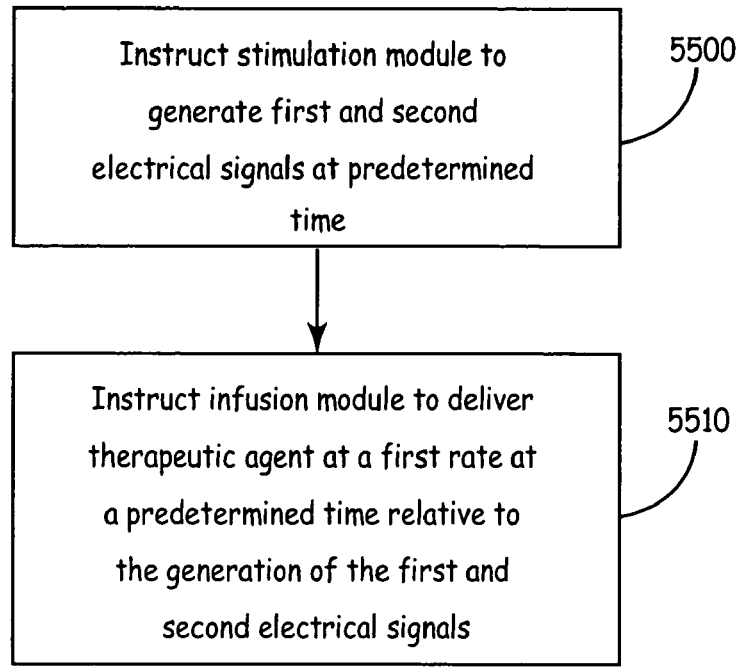
FIGS. 24A-B are flow diagrams of instructing stimulation modules and infusion modules to deliver therapy in a coordinated manner.
Figure 24B:
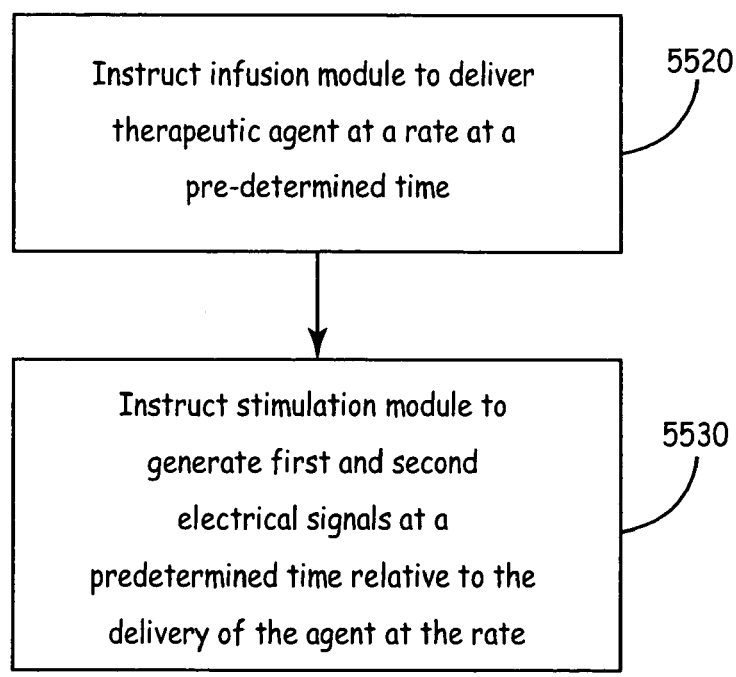

Control unit 5400 as discussed above with regard to FIGS. 22 and 23 may be a programmer 4000, 5050 capable of providing instructions to both stimulation module 5300 and infusion module 5310. The timing of delivery of particular stimulation signals in a stimulation module 5300 and infusion parameters in an infusion module 5310 may be coordinated by such a programmer 4000, 5050 at the time the programmer 4000, 5050 instructs stimulation module 5300 and infusion module 5310 to deliver stimulation signals or therapeutic agent according to particular parameters over time. Referring to FIGS. 24A-B, programmer 4000, 5050 may instruct stimulation module 5300 to generate first (e.g., low frequency) and second (e.g., high frequency) signals at a predetermined time or in a predetermined pattern (5500). Programmer 4000, 5050 may then instruct, either concurrently or at a separate time, infusion module 5310 to deliver therapeutic (e.g., pain treating) agent at a first rate at a predetermined time relative to the generation of the first and second signals (5510). Of course, programmer 4000, 5050 may instruct infusion module 5310 to deliver a therapeutic agent at a rate at a predetermined time (5520) and instruct stimulation module 5300 to generate first and second electric signals at a predetermined time relative to the delivery of the agent at the rate (5530), as show in FIG. 24B. To facilitate delivery of stimulation and infusion therapies in a coordinated fashion, it may be desirable to synchronize stimulation module and infusion module. Such synchronization can occur through any known or future developed technique. Examples of suitable methods for synchronizing two implanted devices are discussed in, e.g., published patent application US20040133390A1: "Synchronization and calibration of clocks for a medical device and calibrated clock."

Programmer 4000, 5050 control unit 5400 may be a physician programmer unit or a patient programmer unit. For example, control unit 5400 may be a patient programmer 4000, 5050 capable of administering patient controlled analgesia (see, e.g. U.S. Patent Application No. 20030204274, published on Oct. 30, 2003). When a patient 15 has breakthrough pain, the patient may request delivery of enhanced pain therapy. When patient 15 requests such therapy using a programmer 4000, 5050, programmer may instruct both the stimulation unit 5300 and infusion unit 5310 to deliver therapy at altered (relative to basal therapy) parameters. For example, if infusion module 5310 contains a μ-opioid agonist to be delivered intrathecally, a patient request for additional therapy may result in the programmer instructing infusion module 5310 to deliver a bolus of μ-opioid agonist, such as morphine, at a particular rate at and for a particular time. Programmer 4000, 5050 may also substantially simultaneously or sequentially instruct stimulation module 5300 to deliver a low frequency stimulation signal for a period of time relative to the administration of the bolus of μ-opioid agonist to enhance the pain treating effect of the bolus.

While not shown, it will be understood that one or more sensors may be employed to effectuate coordinated delivery of pain treating agent therapy and stimulation therapy. By way of example, control unit 1010 of IPG 14 or control module 5330 of stimulation module 5300 may be operably coupled to a sensor capable of detecting the presence or amount of a pain treating agent and may adjust stimulation therapy output based on whether a pain treating agent or an amount of a pain treating agent is present at a location in a patient 15. As another example, control unit 5040 of infusion device 5000 or control module 5350 of infusion module 5310 may be operably coupled to a sensor capable of detecting the presence of a high frequency or low frequency signal (optionally employing appropriate bandwidth filters as necessary or desired) and may adjust infusion therapy output based on whether a high or low frequency signal is being applied at a location in a patient 15.

Coordination of System Components

Coordination of therapy delivery between stimulation module 5300 and infusion module 5310 may occur in a variety of manners. FIGS. 25-30 show a few examples of how such coordination may occur.

Figure 25:
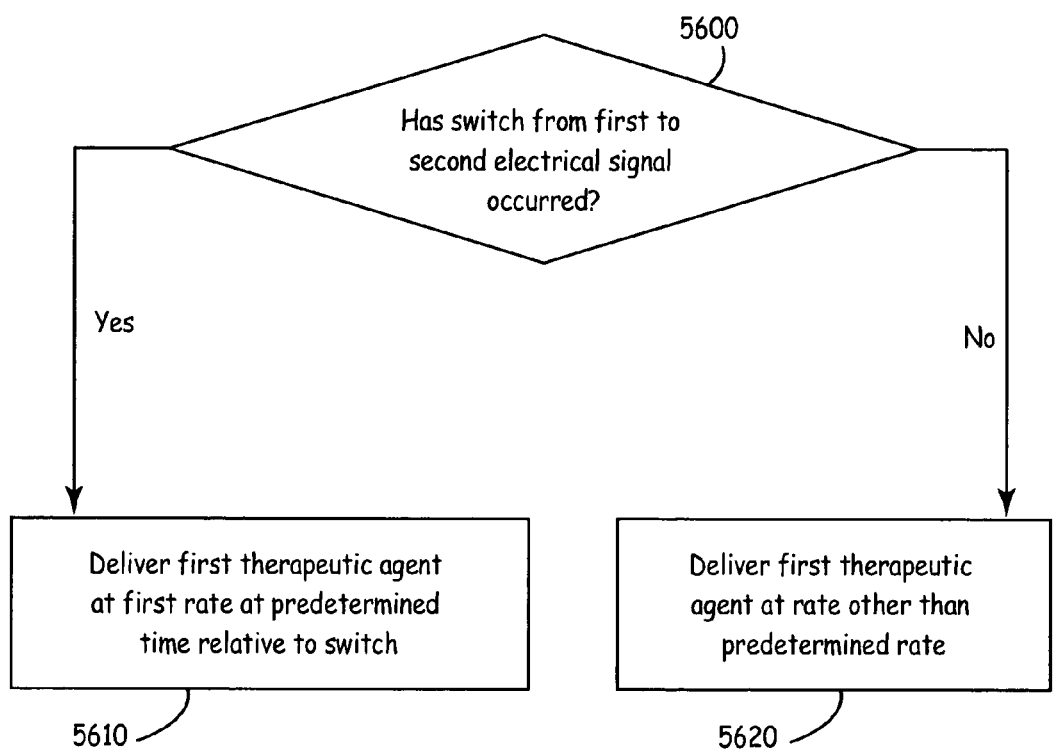
FIGS. 25-30 are flow diagrams of coordinated delivery of stimulation therapy and pain treating agent therapy.
Figure 26:
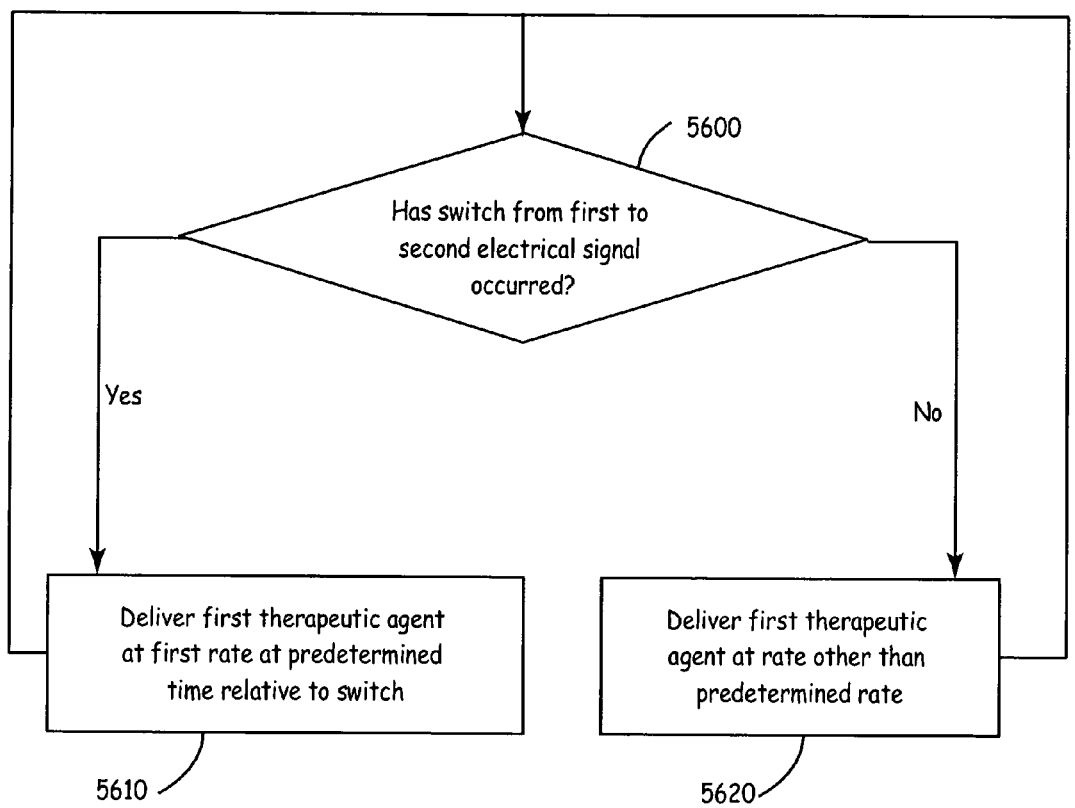

FIG. 25 shows an example suitable for a system comprising a stimulation module 5300 and an infusion module 5310. As shown in FIG. 25, a determination may be made as to whether a switch from generation of a first electrical signal (e.g., low frequency) to a second electrical signal (e.g., high frequency) has occurred (5600). If such a switch has occurred a change in infusion parameter for delivering a first therapeutic agent may be made at a predetermined time relative to the switch (5610). If no such switch has occurred, the infusion parameters associated with the first therapeutic agent may remain unchanged, which may mean that no agent is delivered (5620). Such a change in infusion rate relative to a switch in stimulation parameters may occur one time (e.g., as with a patient programmer request for additional pain therapy) or may occur in a continuous manner, as shown in FIG. 26, indefinitely or for a defined period of time. It will be understood that the process outlined above can readily be adapted to systems including two infusion modules 5310, 5310A or an infusion module 5310 including two reservoirs 5020, 5020A such that a first therapeutic agent is delivered if no switch has occurred and a second therapeutic agent is delivered is a switch has occurred.

Figure 27:
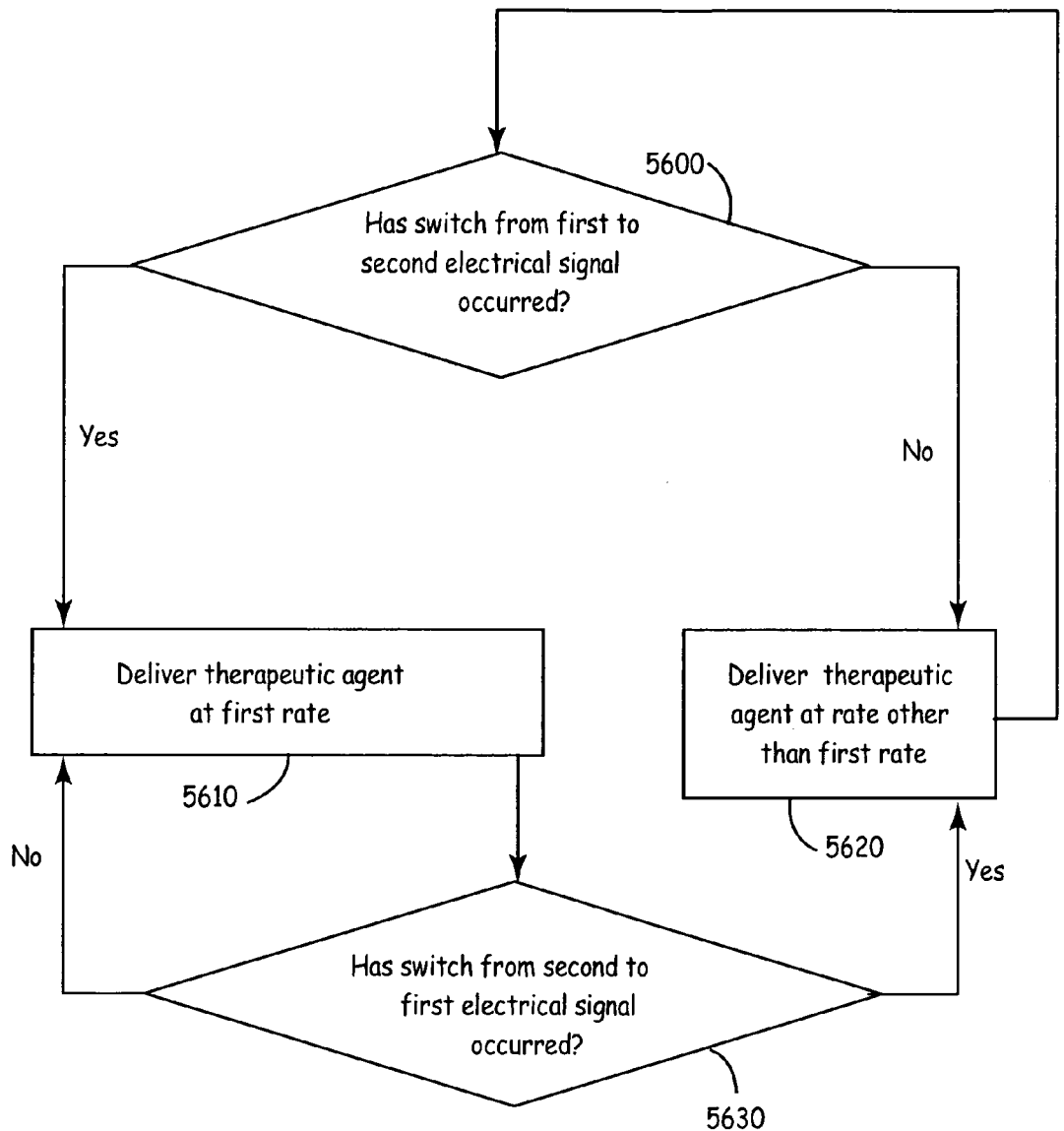

FIG. 27 refers to a process that substantially incorporates the process shown in FIG. 26 and adds a determination as to whether a switch from a second electrical signal (e.g., high frequency) to a first electrical signal (e.g., low frequency) has occurred (5630). As with the process discussed with regard to FIG. 26, if a switch from a first to second signal has occurred (5600), a change in infusion parameter for delivering a first therapeutic agent may be made at a predetermined time relative to the switch (5610). As shown in FIG. 27, if a switch from generation of a second electrical signal to generation of a first electrical signal has occurred (5630), a change in infusion delivery rate (e.g., return to default or basal rate) of first therapeutic agent occurs at a predetermined time relative to the switch (5620) until a switch from first to second electrical signals occurs again (5600).

Figure 28:
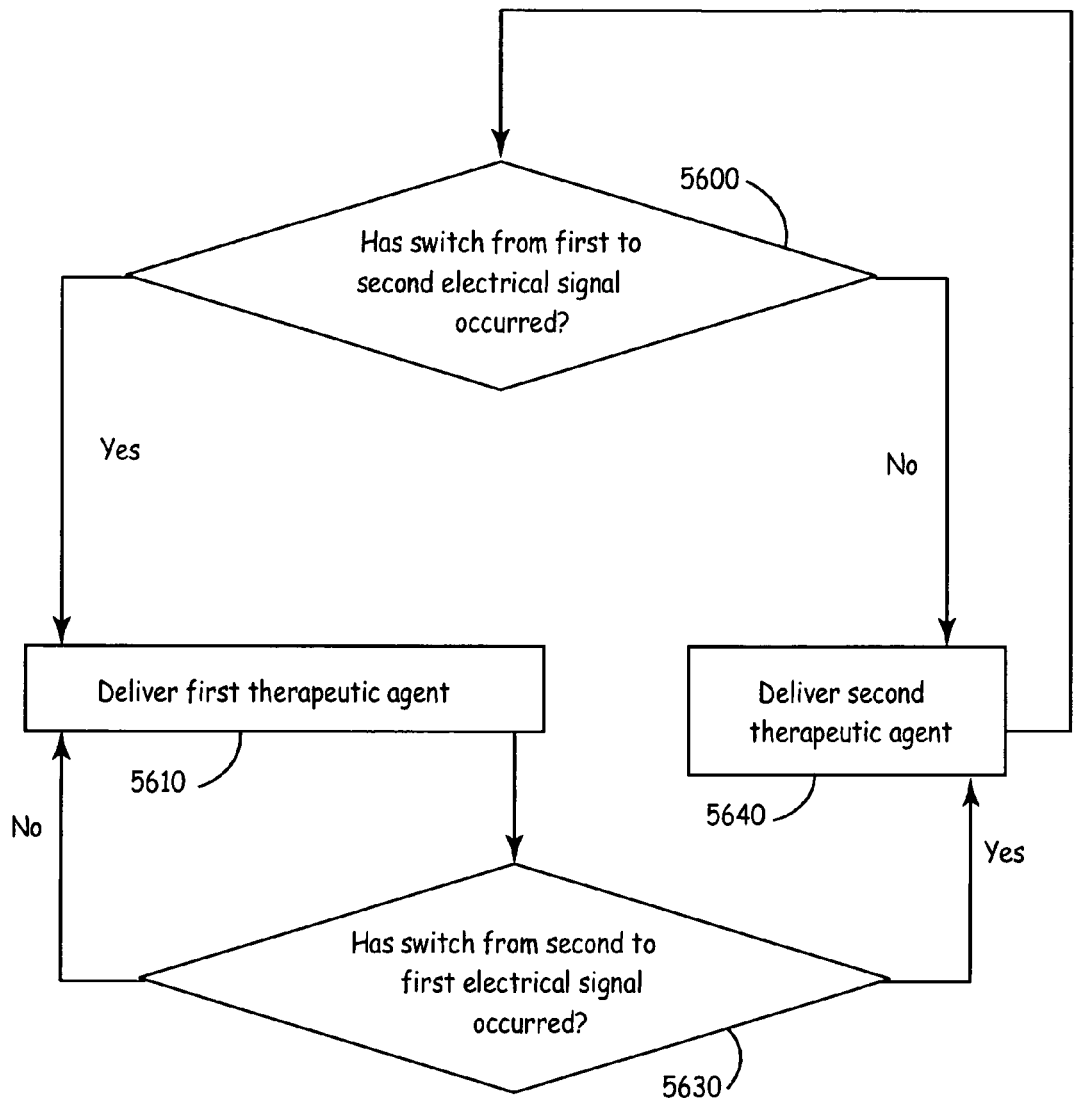

FIG. 28 shows a process suitable for a system including two infusion modules 5310, 5310A or an infusion module 5310 having two reservoirs 5020, 5020A, but otherwise is similar to the process shown in FIG. 27. As with the process discussed with regard to FIGS. 26-27, if a switch from a first to second signal has occurred (5600), a change in infusion parameter for delivering a first therapeutic agent may be made at a predetermined time relative to the switch (5610). As shown in FIG. 28, if a switch from generation of a second electrical signal to generation of a first electrical signal has occurred (5630), a second therapeutic agent can be delivered at a predetermined time relative to the switch (5640) until a switch from first to second electrical signals occurs again (5600), in which case the first therapeutic agent is again delivered with the prior infusion parameters at a predetermined time relative to the switch (5610). It will be understood that a switch from first to second stimulation signals (5600) may stop or return to default or basal rate infusion of the second therapeutic agent and that a switch from second to first stimulation signals (5630) may stop or return to default or basal rate infusion of the first therapeutic agent.

Figure 29:
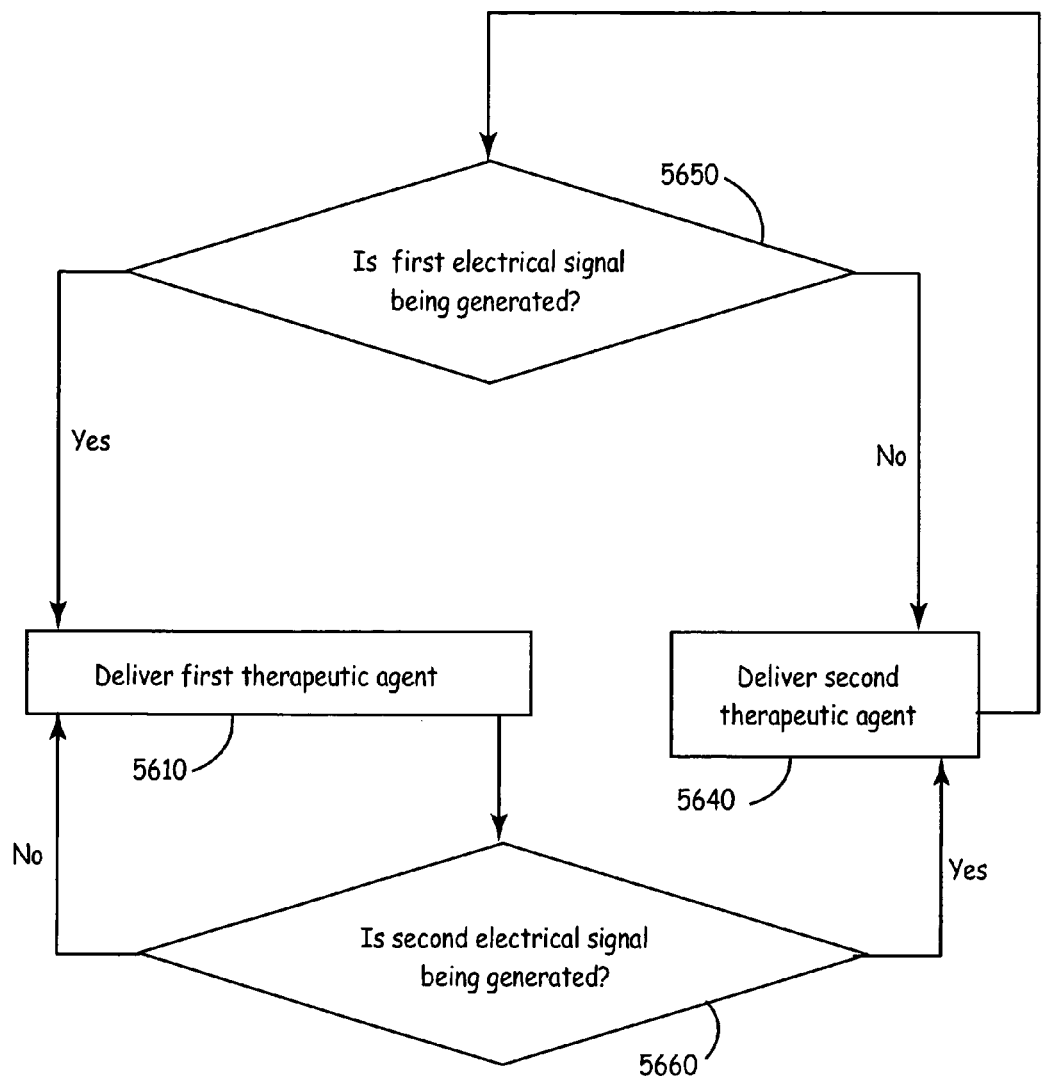

As shown in FIG. 29, the change in infusion parameters of the first therapeutic agent (5610) or the delivery of the second therapeutic agent at a predefined infusion rate (5640) or of the first agent at a different rate (5620) may be coordinated with whether a first electrical signal is being generated (5650) or whether a second electrical signal is being generated (5660) rather than whether a switch from first to second signal (5600) or switch from second to first electrical signal (5630), as discussed with regard to FIGS. 25-28. For example, a determination as to whether a first (5650) or second (5660) electrical signal is being generated may occur at a time when a stimulation module 5300 and an infusion module 5310 are being programmed or may occur at a time during operation of the stimulation module 5300.

Figure 30:
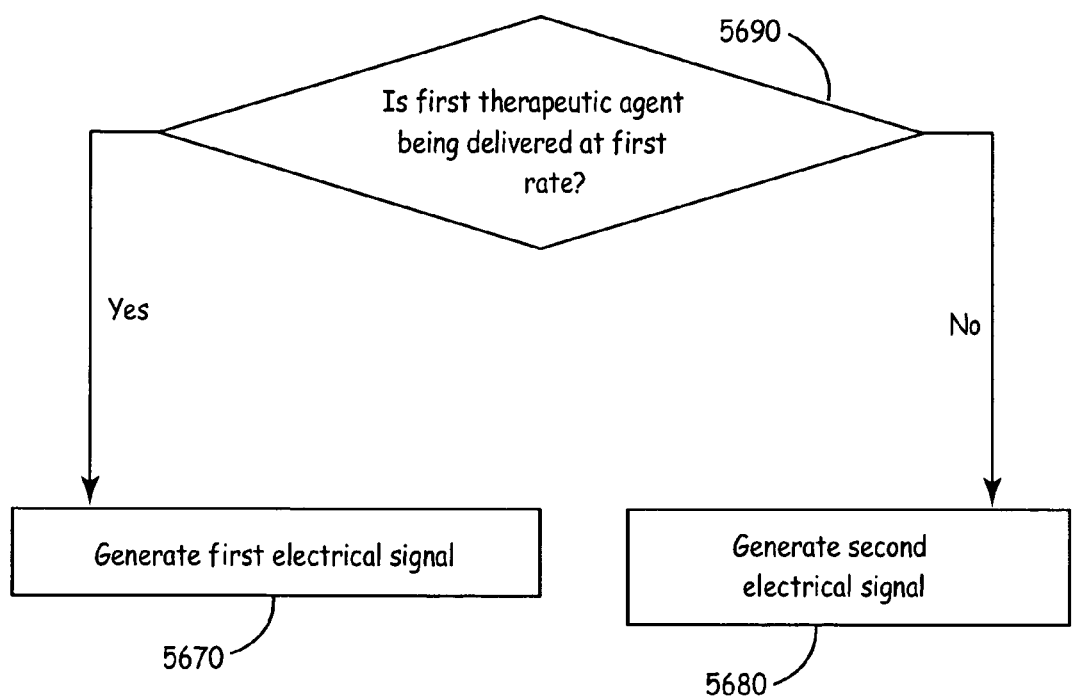

As shown in FIG. 30, a stimulation module 5300 may respond or be programmed to generate a first (5670) or second (5680) electrical signal at a predetermined time relative to whether a first therapeutic agent is being delivered or being delivered at a particular rate (5690). It will be understood that each of the processes discussed with regard to FIGS. 25-29 may readily be modified according to the process described with regard to FIG. 30 such that stimulation module 5300 output is modified based on status of pain treating agent delivery.

All patents, patent applications, technical papers, publications, and devices cited herein are hereby incorporated by reference herein, each in its respective entirety. As those of ordinary skill in the art will readily appreciate upon reading the description herein, at least some of the devices and methods disclosed in the patents and publications cited herein may be modified advantageously in accordance with the teachings of the present invention.

We claim:
1. A system comprising:
   a pulse generator configured to alternate between generation of a first electrical signal and generation of a second electrical signal;
   a first infusion device configured to deliver a first therapeutic agent at a first rate at a first predetermined time that is a first predetermined time interval before or after a time when the pulse generator switches from generation of the first signal to generation of the second signal; and a control unit configured to coordinate the delivery of the first therapeutic agent at the first rate from the first infusion device with the switch from the generation of the first signal to the generation of the second signal.

2. The system of claim 1, wherein the control unit provides information to the infusion device regarding when the pulse generator switches from generation of the first signal to generation of the second signal.

3. The infusion system of claim 1, wherein the control unit instructs the first infusion device when to deliver the first therapeutic agent.

4. The system of claim 1, wherein the control unit is an external programmer unit.

5. The system of claim 4, wherein the external programmer unit provides instructions regarding therapy delivery to both the pulse generator and the first infusion device.

6. The system of claim 5, wherein the external programmer informs the first infusion device regarding when the pulse generator will switch from generation of the first signal to generation of the second signal at the time the programmer provides instructions regarding therapy to the first infusion device.

7. The system of claim 1, wherein the control unit and the first infusion device are housed within a single housing.

8. The system of claim 7, wherein the control unit is configured to communicate wirelessly with the pulse generator.

9. The system of claim 1, wherein the pulse generator and the control unit are configured to communicate wirelessly.

10. The system of claim 9, wherein the first infusion device and the control unit are configured to communicate wirelessly.

11. The system of claim 1, wherein the first infusion device and the control unit are configured to communicate wirelessly.

12. The system of claim 1, wherein the first infusion device delivers the first therapeutic agent at a second rate at a second predetermined time that is a second predetermined time interval before or after the time when the pulse generator switches from generation of the first signal to generation of the second signal, and wherein the control unit is further configured to coordinate the delivery of the first therapeutic agent at the second rate from the first infusion device with the switch from the generation of the first signal to the generation of the second signal.

13. The system of claim 1, wherein the first infusion device delivers the first therapeutic agent at a second rate at a second predetermined time that is a second predetermined time interval before or after a time when the pulse generator switches from generation of the second signal to generation of the first signal, and wherein the control unit is further configured to coordinate the delivery of the first therapeutic agent at the second rate from the first infusion device with the switch from the generation of the second signal to the generation of the first signal.

14. The system of claim 1, further comprising a second infusion device that delivers a second therapeutic agent at a second predetermined time that is a second predetermined time interval before or after the time when the pulse generator switches from generation of the first signal to generation of the second signal,
wherein the control unit is further configured to coordinate the delivery of the second therapeutic agent from the second infusion device with the switch from the generation of the first signal to the generation of the second signal, and wherein the second predetermined time is the same or different than the first predetermined time.

15. The system of claim 1, further comprising a second infusion device that delivers a second therapeutic agent at a second predetermined time that is a second predetermined time interval before or after a time when the pulse generator switches from generation of the second signal to generation of the first signal, wherein the control unit is further configured to coordinate the delivery of the second therapeutic agent from the second infusion device with the switch from the generation of the second signal to the generation of the first signal.

16. The system of claim 1, further comprising a first reservoir and a second reservoir operably coupled to the first infusion device, the first reservoir being configured to house the first therapeutic agent.

17. The system of claim 16, wherein the second reservoir is configured to house a second therapeutic agent.

18. The system of claim 17, wherein the first infusion device delivers the second therapeutic agent at a second predetermined time that is a second predetermined time interval before or after the time when the pulse generator switches from generation of the first signal to generation of the second signal, wherein the control unit is further configured to coordinate the delivery of the second therapeutic agent from the first infusion device with the switch from the generation of the first signal to the generation of the second signal, and wherein the first predetermined time and the second predetermined time is the same or different.

19. The system of claim 17, wherein the first infusion device delivers the second therapeutic agent at a second predetermined time that is a second predetermined time interval before or after a time when the pulse generator switches from generation of the second signal to generation of the first signal, wherein the control unit is further configured to coordinate the delivery of the second therapeutic agent from the first infusion device with the switch from the generation of the second signal to the generation of the first signal.

20. A system comprising:

a pulse generator configured to alternate between generation of a first electrical signal and generation of a second electrical signal; and an infusion device configured to deliver a first therapeutic agent at a predetermined time that is a predetermined time interval before or after a time when the pulse generator switches from generation of the first signal to generation of the second signal.

21. A method comprising:

identifying whether a first predetermined electrical signal is being generated by an implantable pulse generator via a control unit; and instructing an infusion device to deliver a therapeutic agent at a rate if the predetermined electrical signal is being generated via the control unit, wherein the control unit is separate from the implantable pulse generator and the infusion device.

* * * * *